US010054961B2

(12) United States Patent
Ismagilov et al.

(10) Patent No.: US 10,054,961 B2
(45) Date of Patent: Aug. 21, 2018

(54) METHODS FOR MANIPULATING SPACING BETWEEN MICRODROPLETS FLOWING IN A MICROFLUIDIC SYSTEM

(71) Applicant: The University of Chicago, Chicago, IL (US)

(72) Inventors: Rustem F. Ismagilov, Chicago, IL (US); Bo Zheng, Chicago, IL (US); Cory John Gerdts, Chicago, IL (US)

(73) Assignee: The University of Chicago, Chicago, IL (US)

( * ) Notice: Subject to any disclaimer, the term of this patent is extended or adjusted under 35 U.S.C. 154(b) by 385 days.

(21) Appl. No.: 14/184,312

(22) Filed: Feb. 19, 2014

(65) Prior Publication Data
US 2014/0202546 A1    Jul. 24, 2014

Related U.S. Application Data

(63) Continuation of application No. 11/174,298, filed on Jul. 1, 2005, now Pat. No. 9,477,233, which is a
(Continued)

(51) Int. Cl.
*B01J 19/00* (2006.01)
*G01N 1/38* (2006.01)
(Continued)

(52) U.S. Cl.
CPC ......... *G05D 7/0694* (2013.01); *B01F 5/0471* (2013.01); *B01F 13/0071* (2013.01);
(Continued)

(58) Field of Classification Search
CPC ........ C12Q 2565/629; C12Q 2563/159; C12Q 2537/143; C12Q 3/00; B01L 3/502784;
(Continued)

(56) References Cited

U.S. PATENT DOCUMENTS 3,640,822 A * 2/1972 Hrdina ................... G01N 35/08
  210/198.2
3,743,103 A * 7/1973 Isreeli ................ B01D 17/0208
  210/532.1
(Continued)

FOREIGN PATENT DOCUMENTS

WO    9802237 A1    1/1998

OTHER PUBLICATIONS

Tan et al.,"Design of microfluidic channel geometries for the control of droplet volume, chemical concentration, and sorting†", Lab Chip, Jul. 2004, v. 4, pp. 292-298.*
(Continued)

*Primary Examiner* — Jennifer Wecker
(74) *Attorney, Agent, or Firm* — Brown Rudnick LLP; Thomas C. Meyers

(57) ABSTRACT

The present invention provides manipulation of spacing between microdroplets flowing in a microfluidic system. The manipulation includes increasing and/or decreasing spacing between a pair of adjacent droplets of a sample fluid flowing in an immiscible carrier fluid within a main microfluidic channel. The main microfluidic channel includes a region having one or more side branch channels. The spacing between the pair of droplets flowing through the region can be increased or reduced with either the addition of or removal of immiscible carrier fluid between the adjacent droplets via at least one of the side branch channels, wherein the pair of droplets remain intact while flowing through the region and continue to flow within the main microfluidic channel downstream of the region.

13 Claims, 11 Drawing Sheets

Related U.S. Application Data continuation of application No. 11/082,187, filed on Mar. 16, 2005, now Pat. No. 7,655,470.

(60) Provisional application No. 60/623,261, filed on Oct. 29, 2004, provisional application No. 61/585,801, filed on Jul. 2, 2004.

(51) Int. Cl.
*G01N 35/10* (2006.01)
*G05D 7/06* (2006.01)
*G01N 35/08* (2006.01)
*B01F 13/00* (2006.01)
*B01F 5/04* (2006.01)
*B01L 3/02* (2006.01)
*B01L 3/00* (2006.01)

(52) U.S. Cl.
CPC ......... *B01J 19/0046* (2013.01); *B01L 3/0293* (2013.01); *B01L 3/502784* (2013.01); *G01N 1/38* (2013.01); *G01N 35/08* (2013.01); *B01J 2219/0059* (2013.01); *B01J 2219/00522* (2013.01); *B01J 2219/00585* (2013.01); *B01J 2219/00599* (2013.01); *B01L 3/502746* (2013.01); *B01L 2200/0673* (2013.01); *B01L 2300/0816* (2013.01); *B01L 2300/0838* (2013.01); *B01L 2300/0864* (2013.01); *B01L 2300/0867* (2013.01); *B01L 2400/0487* (2013.01); *G01N 2035/1034* (2013.01); *Y10T 137/0318* (2015.04)

(58) Field of Classification Search
CPC ..... B01L 2200/0673; B01L 2300/0816; B01L 2400/0487; B01L 2300/0864; B01L 3/502746; B01L 2300/0867; B01L 3/502175; B01L 2300/0838; B01L 3/0293; B01L 3/00; B01F 13/0071; B01F 5/0471; B01J 19/0046; B01J 2219/00522; B01J 2219/00585; B01J 2219/0059; B01J 2219/00599; G01N 1/38; G01N 2035/1034; G01N 35/08; G05D 7/0694; Y10T 137/0318

See application file for complete search history.

(56) References Cited

U.S. PATENT DOCUMENTS

| | | | |
|---|---|---|---|
| 4,215,092 A | 7/1980 | Suovaniemi et al. | |
| 7,129,091 B2 * | 10/2006 | Ismagilov | B01F 5/0646 436/34 |
| 7,294,503 B2 | 11/2007 | Quake et al. | |
| 7,655,470 B2 | 2/2010 | Ismagilov et al. | |
| 7,901,939 B2 | 3/2011 | Ismagilov et al. | |
| 8,304,193 B2 | 11/2012 | Ismagilov et al. | |
| 2002/0058332 A1 * | 5/2002 | Quake | B01L 3/502761 435/288.5 |
| 2004/0224380 A1 | 11/2004 | Chou et al. | |

OTHER PUBLICATIONS

Tice et al. "Formation of Droplets and Mixing in Multiphase Microfluidics at Low Values of the Reynolds and the Capillary Numbers", Langmuir, 2003, v. 19, pp. 9127-9133.*

Engl et al., "Droplet Traffic at a Simple Junction at Low Capillary Numbers", Phys. Reviews Lett., Nov. 11, 2005, v. 95, 208304-1-208304-2.*

Leng et al., 2010, Agarose droplet microfluidics for highly parallel and efficient single molecule emulsion PCR, Lab Chip 10(21):2841-3.

Nakano et al., 2003, Single-molecule PCR using water-in-oil emulsion, Journal of Biotechnology 102(2):117-124.

Gambi et al., 1997, Dynamic percolation in fluorinated water-in-oil microemulsions, Physical Review E 56(4):4356-4363.

Adamson et al., "Production of arrays of chemically distinct nanolitre plugs via repeated splitting in microfluidic devices", Lab Chip, 2006 6, pp. 1178-1186.

Thorsen et al. "Dynamic Pattern Formation in a Vesicle-Generating Microfluidic Device", Phys. Rev. Lett., 2001, v. 86, No. 18, pp. 4163-4166.

Emmer and Roeraade, "Wall deactivation with fluorosurfactants for capillary electrophoretic analysis of biomolecules" Electrophoresis, 2001, v. 22, pp. 660-665.

* cited by examiner a)

b)

c)

A

B

METHODS FOR MANIPULATING SPACING BETWEEN MICRODROPLETS FLOWING IN A MICROFLUIDIC SYSTEM

RELATED APPLICATIONS

The present application is a continuation under 35 U.S.C. § 120 of U.S. Ser. No. 11/082,187, filed Mar. 16, 2005, pending, incorporated herein by reference. The present application is also related to and claims priority pursuant to 35 U.S.C. § 119 to U.S. Serial No. 60/623,261 (filed Oct. 29, 2004) and 60/585,801 (filed Jul. 2, 2004); both of which are incorporated herein by reference in their entirety.

FEDERALLY SPONSORED RESEARCH OR DEVELOPMENT

This work was supported by the NIH (R01 EB001903). Additionally, some of this work was performed at the MRSEC microfluidic facility funded by the NSF. The government may have certain rights in this application.

TECHNICAL FIELD

The present invention relates to the field of microfluidics. This invention provides microfluidic technology enabling rapid and economical manipulation of reactions on the sub-femtoliter to milliliter scale.

BACKGROUND OF THE INVENTION

The ability to run a large number of reactions using minimal reagent is desirable. Various solutions to this goal have been proposed, including robotics, microfluidics, combinatorial chemistry in 96-well plates, etc. The application of these methods to a variety of reactions has been proposed.

For example, membrane proteins play a crucial role in many cellular and physiological processes critical to human health. Determination of the structure of membrane proteins is a critical step in the understanding of their function. X-ray crystallography is a powerful tool for the determination of the structure of membrane proteins. Crystallization conditions for membrane proteins are determined by a large number of screening experiments. Membrane proteins are often difficult to produce, therefore miniaturization of the crystallization screens is essential for accelerating the structural studies. Crystals of membrane proteins are often fragile and can be damaged by handling, therefore technologies are needed to allow for direct in situ testing of the diffraction quality of crystals. Handling nanoliter volumes of solutions of membrane proteins is challenging due to their high viscosity and low surface tension.

WO 04/104228 describes the use of microfluidic structures for high throughput screening of protein crystallization. In one embodiment, an integrated combinatorially mixing chip allows for precise metering of reagents to rapidly create a large number of potential crystallization conditions, with possible crystal formation observed on chip. In an alternative embodiment, the microfluidic structures may be utilized to explore phase space conditions of a particular protein/crystallizing agent combination, thereby identifying promising conditions and allowing for subsequent focused attempts to obtain crystal growth. Unfortunately, this system is expensive to operate; the combinatorially mixing chips are significantly more expensive than traditional crystallography plates; the combinatorially mixing chips are water and gas permeable; and are incompatible with organic solvents. Thus, a need exists for rapid, economical crystallization of membrane proteins.

BRIEF SUMMARY OF THE INVENTION

This invention provides a method of conducting a large number of reactions in parallel, such as crystallizations or assays, allowing rapid and economical reactions.

This invention is particularly well suited for crystallization of proteins, biomolecules, complexes of biomolecules with bound ligand, etc. This invention allows direct testing of the diffraction quality of crystals. The present invention can also be applied in the field of combinatorial chemistry, allowing the monitoring of both kinetics and reaction products.

The present invention has one or more of the following attractive features: (1) The method is scalable—increasing the number of reagents used in a screen does not require more complex fabrication, just a longer receiving component. (2) The method in some embodiments may include the use of spacers in three-phase flow. For example, the use of fluorinated carrier fluid can provide protection of plugs and control of the surface chemistry, and the use of gas bubbles can prevent aqueous plugs from merging. (3) Arrays may be pre-fabricated by a range of methods, from simple methods using syringes, to robotics. Pre-fabricated arrays of plugs in capillaries may be stored for months, and can be made sterile or prepared under inert atmosphere, expanding the range of potential applications. (4) The method is very simple for the end user—no sophisticated equipment is required on the user's end except a source of constant flow to drive multiple streams to combine. Overall, this method is attractive for applications in which reagents must be stored and used in a simple, reliable format, such as in diagnostics and detection. In addition, this method may find a wide range of application in chemistry and biochemistry, enhancing and miniaturizing current methods in which reagents in 96-, 384- and 1536-well plates are stored or distributed, such as combinatorial chemistry, protein crystallization, and biochemical assays.

b) Microphotograph of multiple aqueous streams originating from a single delivery channel merging with plugs of red inorganic dye. c) merging of a stream (illustrated by a stream containing protein) with an array of plugs.

Figure 5:
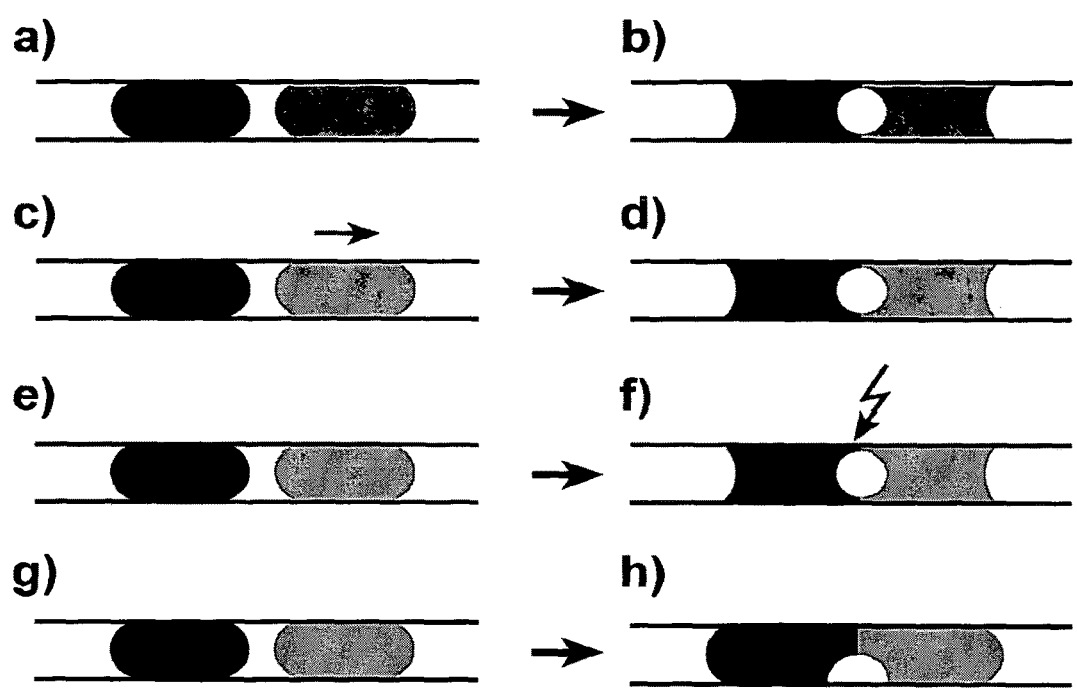

FIG. 5. Schematic diagrams of methods to bring two plugs into contact. a) Plugs in a channel where wetting of the channel by the plug fluid is prevented. b) Plugs in a channel where wetting of the channel by the plug fluid is allowed. c) Plugs in a channel while flow is established and wetting of the channel by the plug fluid is prevented. d) Plugs that are not flowing in a channel and wetting of the channel by the plug fluid is allowed. e) Plugs in a channel with a photo-switchable monolayer that initially prevents wetting. f) Plugs in a channel after the photoswitchable monolayer has been activated with a particular wavelength of light. g) Aqueous plugs inside a holding component. h) A force is applied such that the symmetry is broken and a liquid bridge between the two plugs is formed. The force may be magnetic, electric, optical, or an accelerating force (such as in centrifugation), etc. The force may be exerted on the carrier fluid, the crystallization solutions, or both, depending on the configuration of the experiment. Preferably the force is applied normal to the section of the holding component. If magnetic forces are used, preferably the carrier fluids and the plug fluids have different magnetic properties. If centrifugation is used, preferably the carrier fluids and the plug fluids have different densities, as is the case when aqueous plug fluids and fluorinated carrier fluids are used.

Figure 6:
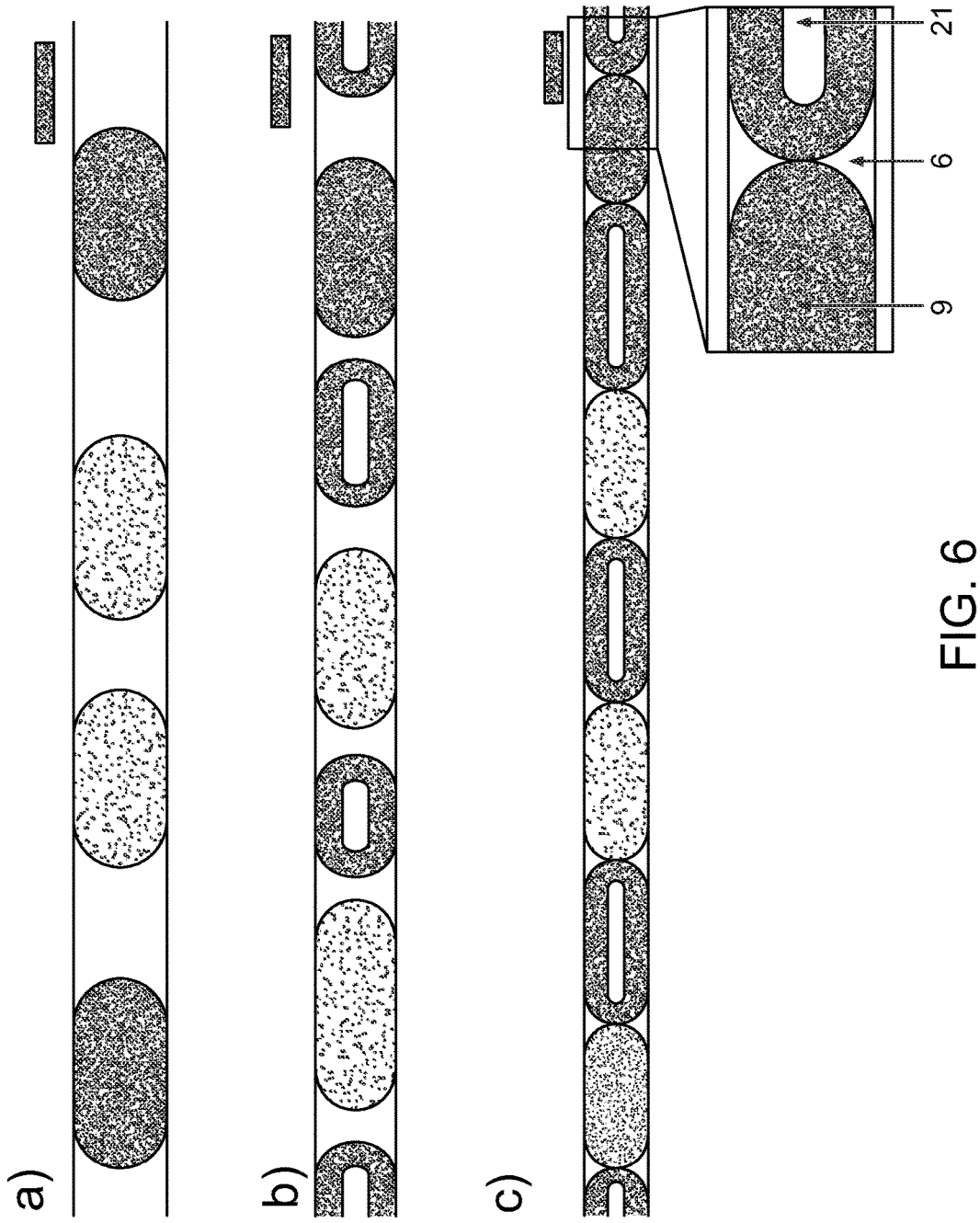

FIG. 6. a) An array of plugs of four different reagents in a capillary. The plugs contain $KMnO_4$, NaCl, $CuSO_4$ and $Fe(SCN)_3$, from left to right. The carrier is a fluorocarbon with surfactant. b, c) An array of plugs of different reagents formed in fluorocarbon and separated by air bubbles (dark) in a capillary. In (b) the aqueous plugs are separated from air bubbles by a spacer of fluorocarbon, preventing cross-communication between the plugs. The scale bars are 200 µm.

Figure 7:
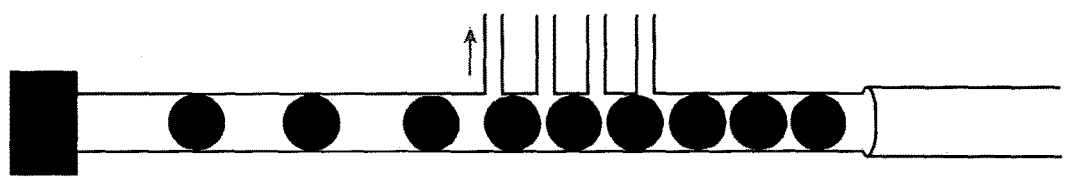
Figure 7:
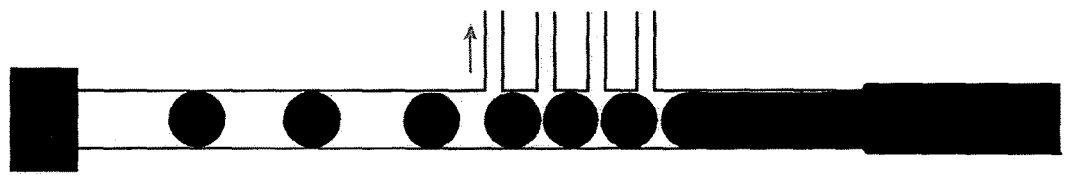

FIG. 7. A schematic microfluidic setup for controlling distances between plugs, and in some cases for merging plugs. The carrier fluid is drained through small side branch channels. (a) The spacing between the plugs decreases accordingly. (b) The carrier fluid is completely removed and all the contents of the plugs merged into a stream of plug fluid.

Figure 8:
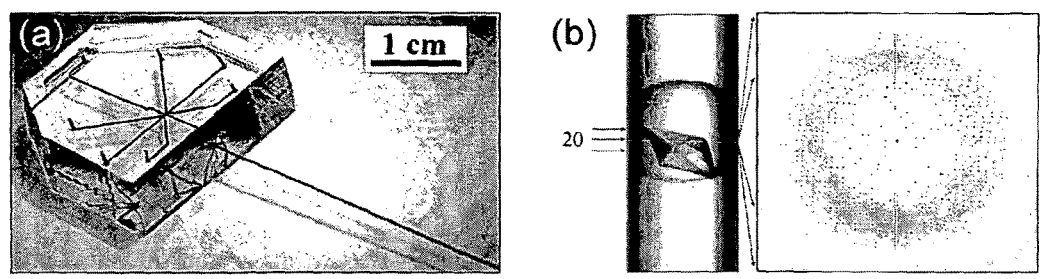

FIG. 8. a) PDMS-glass composite system for protein crystallization. b) Synchrotron diffraction image (right) of a thaumatin crystal (left) grown and diffracted inside a plug in a capillary to yield a structure with better than 1.8 Å resolution (I/σ(I)=4.7 at 1.8 Å).

Figure 9:
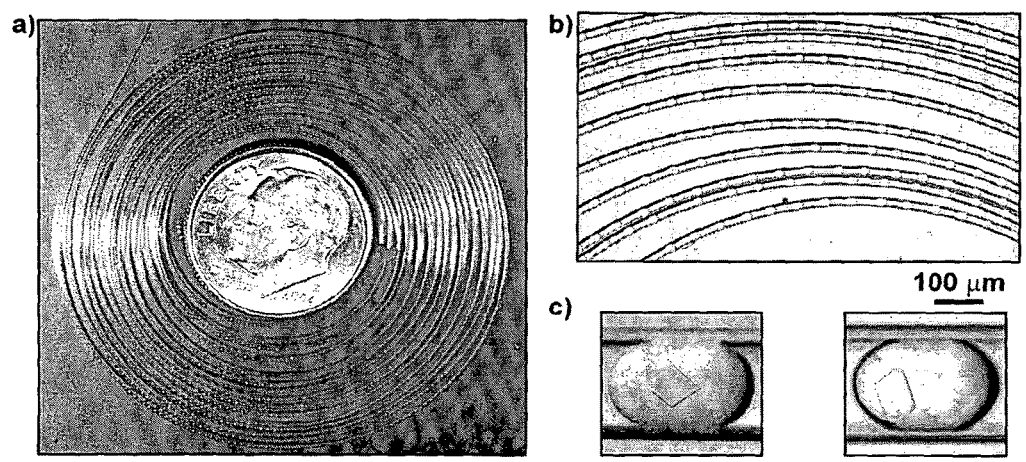

FIG. 9. Crystallization of the membrane protein FAAH. Plug-based microfluidics can be used to crystallize membrane proteins and perform many crystallization trials with small amounts of sample. a) A microphotograph of one meter of Teflon capillary wound around a dime. The capillary contains ~1,000 nanoliter-sized plugs. Only 10 µL of membrane protein solution is needed to set up 1000 crystallization trials. b) A magnified portion of the microphotograph in a) showing plugs in the capillary. c) Two microphotographs of membrane protein (FAAH) crystals grown in plugs.

Figure 10:
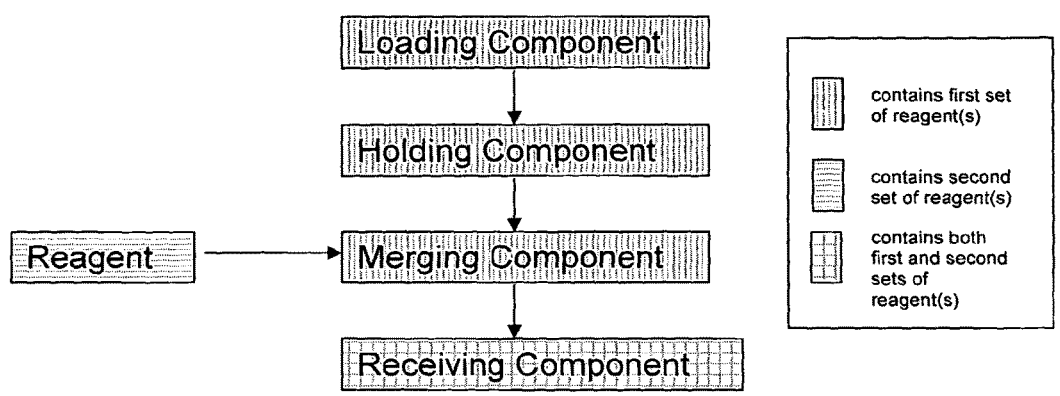

FIG. 10. A flowchart showing one embodiment of the microfluidic system of the present invention. The loading component prepares a linear array of plugs containing a first set of reagents. The loading component is attachable to a holding component such that the array can be transferred with fluid flow. The holding component can be attached to the combining component, such that a second reagent or set of reagents can be introduced into plugs within the array. The array can be moved to a receiving component for further manipulations.

Figure 11:
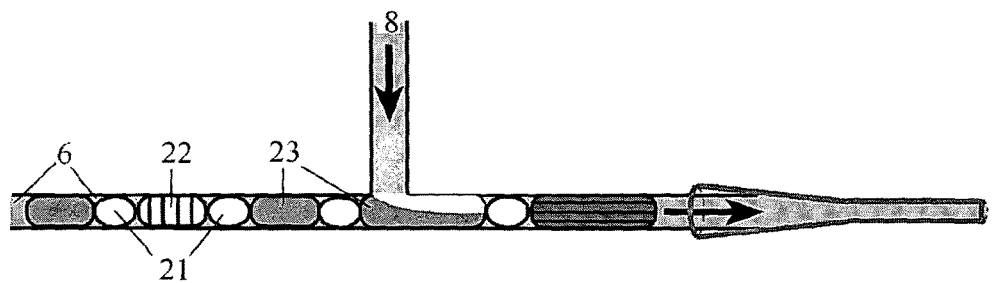

FIG. 11. A schematic illustration of the assay of multiple plugs containing different enzymes against a single protein substrate 8. Each plug containing an enzyme 22 is separated from another plug with a different enzyme by carrier, a spacer 21, and at least one washing plug 23.

Figure 12:
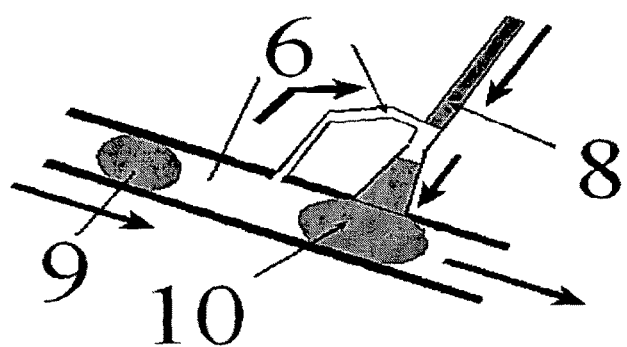

FIG. 12. A schematic illustration of a possible geometry for merging a plug 9 with a stream 8 to created a merged plug 10 without cross-contamination. A short narrow side channel may be used for the carrier 6 to aid in snapping off a volume of the merging stream 8. The volume of the trapezoidal expansion may be used to define the volume of the fluid merged. Other shapes than the trapezoidal expansion may be used to optimize the performance. The main channel shown in bold lines may be made greater in the z-dimension than the other channels shown with thinner lines.

Figure 13:
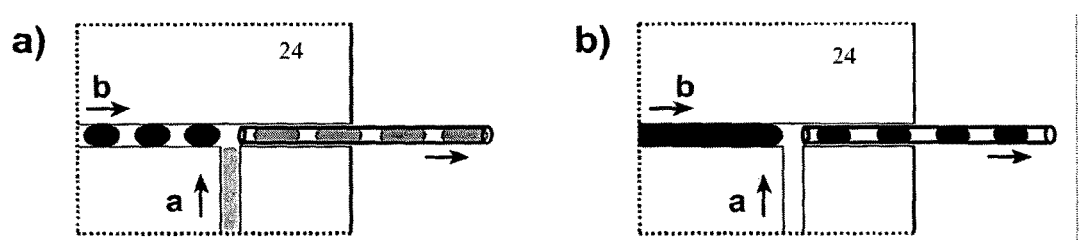

FIG. 13. A simple T-junction in PDMS is fitted with a Teflon capillary. The PDMS chip is fabricated as usual by sealing a piece of PDMS with microfluidic channels to another flat piece of PDMS. Prior to sealing, a Teflon capillary is placed in the channel. The space between the Teflon capillary and square microfluidic channel is then filled with uncured PDMS mixture and cured. The resulting junction can be used to merge an array of preformed plugs with another stream, or to form plugs. Since fluorinated carrier fluids preferentially wet a Teflon surface, the Teflon capillaries do not need surface treatment before use. a) shows an array of preformed plugs (channel b) merging with another stream (channel a). b) shows that to form plugs, an aqueous stream can be pumped in through channel a while the carrier fluid is pumped through channel b. At the junction, aqueous droplets, or plugs, form spontaneously and are transported through the Teflon capillary. This is particularly useful for aqueous detergent solutions, which would not otherwise may be able to form plugs.

Figure 14:
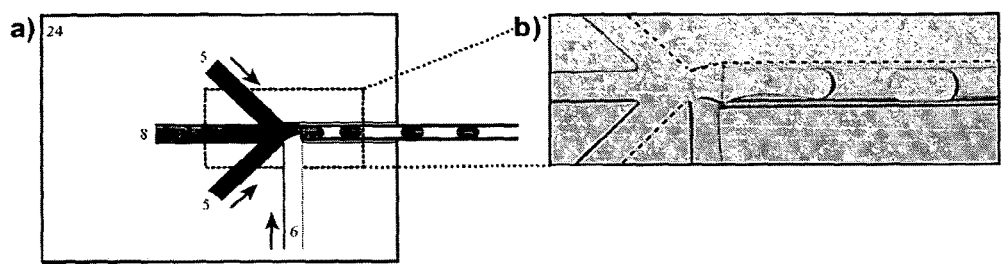

FIG. 14. a) Schematic and b) microphotograph of Teflon capillary-PDMS composite device used for a membrane protein crystallization experiment. Plugs containing membrane protein and precipitants were formed in a stream of immiscible carrier fluid composed of perfluorotrialkylamines. The membrane protein used was the apo form of fatty acid amide hydrolase, the carrier fluid was perfluoro-compound FC-70, and the precipitant was 24% PEG 4000, 0.20 M LiSO4, 0.40 M NaCl, 0.10 M Tris pH=8.2. Flow rates were as follows: carrier fluid—1 µL/min; protein—0.5 µL/min; each precipitant stream—0.25 µL/min.

Figure 15:
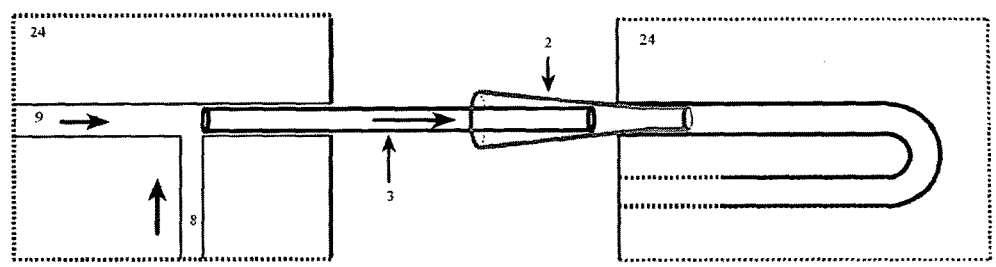

FIG. 15. Tubing or capillaries can also be used to connect several chips 24. For example, plugs 9 may be formed or merged with a stream 8 on one device, and transferred through a tubing and/or a capillary to another chip 24. The use of an inserted capillary 3 to make a connection to one device, and the use of a funnel-shaped adapter 2 to make a connection to another device is shown in the figure. A range of connecting methods may be used in any combination.

Figure 16:
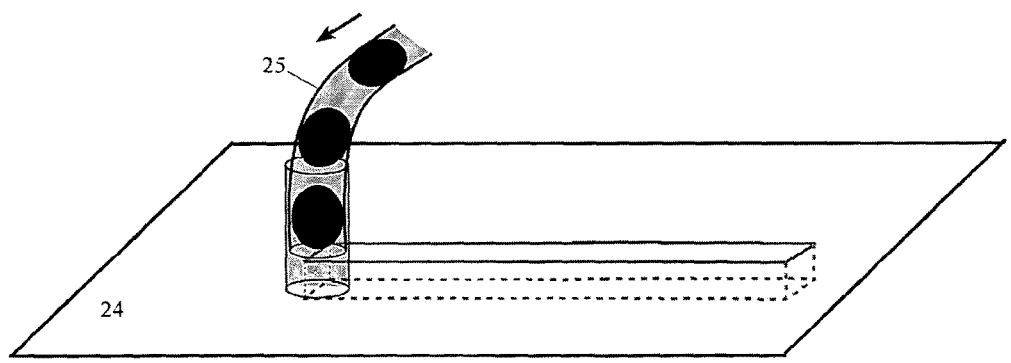

FIG. 16. The connection between tubing 25 and a chip 24 may be out of plane of the chip. Tubing can be connected to the chip through a hole on the microfluidic chip. Preformed arrays of plugs can be transported to the microfluidic chip for further manipulation.

Figure 17:
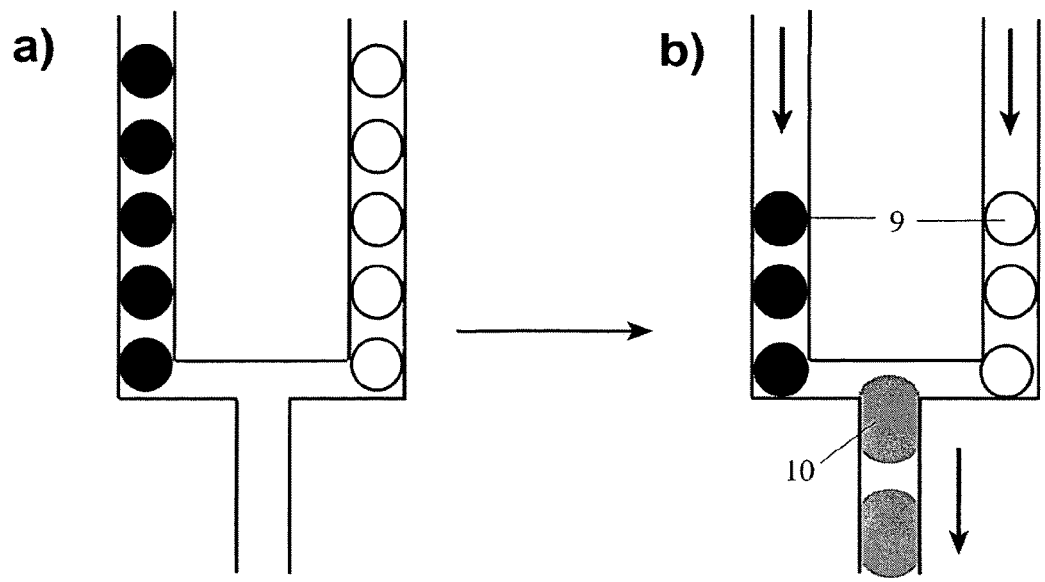

FIG. 17. (a) Two arrays of plugs 9 can be stored in the holding component. The holding component may be configured so that the two arrays of plugs can be merged, as shown in (b). The merged plugs 10 can be then transferred to a combining component for further reactions.

Figure 18:
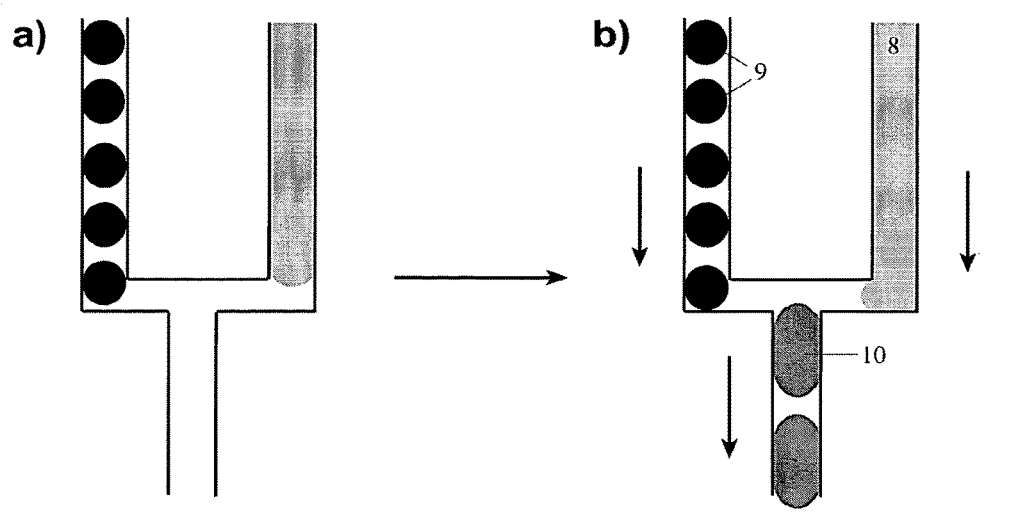

FIG. 18. (a) An array of plugs 9 and a stream 8 may also be stored in the holding component. Merged plugs 10 can be formed prior to transfer to a combining component for further reactions.

DETAILED DESCRIPTION OF THE INVENTION

The present invention provides a system for plug-based microfluidic manipulation of small volumes of solutions. Certain embodiments of the system comprise a loading component, a holding component, a combining component and a receiving component. FIG. 10 illustrates one embodiment of the system of the present invention. The various components can be integrated into a single system or one or more of the components can be detachable from the microfluidic system. For example, each component could be separately detachable—such that the holding component can be a stand alone component that is attachable to both the loading component and the combining component. In another example, the receiving component may be integrated with the combining component Throughout this disclosure the use of the present invention is exemplified by application to protein crystallography. It should be understood that this invention is equally applicable to other reactions.

Plug-based microfluidic manipulation of solutions has been described previously by the present inventors in U.S. Ser. Nos. 10/434,970 and 10/765,718, incorporated herein in their entirety by reference.

Loading Component

The loading component comprises at least one microchannel, which is suitable for forming an array comprising fluid plugs that are separated from one another by a carrier and at least one outlet configured to be able to make a fluid connection with a holding component.

The loading component can be any device capable of filling a holding component with the desired array of plugs separated by the desired carrier fluid or fluids. The process could be carried out manually, for instance with manually operated pipettes or syringes, or through the use of pipetting robots. Alternatively, the loading component can be a microfluidic device with at least one channel and at least one outlet configured to be able to make a fluid connection with a receiving component. The loading component could also be based on the type of devices described by Laura Lane, The Scientist, Volume 18, Issue 1(34), Jan. 19, 2004, that are capable of preparing small volumes of varying solutions. Such devices include, for example, the Agincourt™ system manufactured by Syrrx, Gilson's 925 PC Workstation, deCODE's MatrixMaker™, Matrix Technologies' Hydra® Plus-One System, and the Fluidigm Topaz™ Crystallizer. The loading component may or may not have an integral means for sealing or capping the ends of the holding component.

Holding Component

The holding component is useful for storing and transporting at least one linear array of plugs.

The detachable holding component has at least one microchannel configured so that it can make a fluid connection with the loading component. When the holding component is detached from the loading component, the fluid plugs typically do not immediately merge or mix. The detachable holding component may be a preformed cartridge that may be sold as an independent item of commerce. The terms "holding component" and "preformed cartridge" are used interchangeably in this application. Examples of holding component materials include, but are not limited to, PDMS, glass tubes (such as a capillary), tubing (such as Teflon tubing or polyimide tubing), and composite tubing (for example, a glass capillary coated with polyimide, or Teflon tubing inside a glass capillary). The microchannel of the holding component can have an inner diameter of similar or differing size to the microchannel of the loading component, the combining component or the receiving component. The holding component may be wound, such as in a spiral or a cylinder, and transported with or without a spool, to facilitate handling. Microchannels may be wound, such as in a spiral or a cylinder. For the purposes of this application, the plugs in such configurations are still considered to be arranged in a "linear array".

One embodiment of the present invention is a kit containing a holding component with at least one linear array of plugs. The holding component in the kit may have more than one array of plugs. For example, two arrays of plugs can be stored in the holding component. The holding component may be configured so that the two arrays of plugs can be merged. The merged plugs can be then transferred to the combining component for further reactions. Also, an array of plugs may be stored in the holding component together with a stream of a reagent or solvent. The holding component may be configured to induce merging of the plugs with the stream, and this merged array of plugs may be transferred into the combining component for further reactions. Such a system will be useful, for example, for reactions that involve the generation of unstable species upon mixing of two or more components that are more stable.

In one embodiment, the holding component may be capped or sealed on one or both ends to facilitate storage or transport. If the carrier fluid is not volatile, it may not be necessary to seal or cap the ends. Also, unsealed holding components may transported by submerging one or both ends in carrier fluid.

In some embodiments, especially those where liquid or gas permeability through plastic is an issue for long-term storage, the holding component with the plugs inside can be frozen.

The holding component is ideal for storing reagents in a controlled environment. The holding component can be used to dispense the plugs into another component in the microfluidic system or can be used to dispense the plugs into a volume or onto a surface (such as a well plate (e.g. commercially available 96-, 384- or 1536-well plates), microscope slides, cell culturing media, etc). If the plug fluid has a low surface tension (like a fluorocarbon), then the plugs can be dispensed simply by dripping the plugs from the holding component. To facilitate dispensing of single plugs, markers or spacers could be used to aid the user in visualizing single drops. In addition, as the dispensing is taking place, spacers may facilitate the break up of the fluid into parts containing the individual plug fluids. A volatile carrier fluid may be used so the carrier fluid is removed by evaporation. Examples of volatile carrier fluids include butanes, perfluorobutanes and perfluoropentanes.

Holding components are ideal for preparing crystallization experiments. For microbatch experiments, the preloaded cartridges may contain precipitant plugs of varying concentrations. These plugs can be merged with a stream of protein solution to set up crystallization screens. For vapor diffusion experiments, preloaded cartridges of alternating plugs (precipitant alternating with desiccant)) may be used.

For vapor diffusion experiments, the system can be configured such that only the precipitant plugs will merge with the protein stream. To conduct free interface diffusion experiments, instead of merging the protein stream with the plugs of varying reagent, the protein stream forms its own plugs which, after the flow is stopped, are allowed to come into contact with adjacent precipitant plugs, forming the free interface. Holding components are also ideal for conducting assays, reactions, screens, etc.

In order to further prevent the merging of the plugs in the preloaded cartridge, each pair of plugs can be separated by a spacer (as described below).

Each plug in the linear array of fluid plugs in the holding component can comprise at least one solvent and at least one reagent. Mixtures of solvents and reagents can be used. In some embodiments, each plug comprises a different concentration of the same reagent or mixture of reagents. In other embodiments, at least two plugs in the linear array comprise different reagents. The components of a linear array can be chosen to span a certain portion of chemical space. As used herein, chemical space encompasses all possible small organic and inorganic molecules and materials, including those present in biological systems, at all possible concentrations. A linear array can span a portion of chemical space when the plugs comprising the array are chosen so that they share a similar feature (such as similar molecular masses, lipophilicities, topological features, reactive groups, core structures, etc.). Compounds with similar features have already been grouped into various existing databases (see e.g., Dobson, Nature, 432:824-828 (2004) and Feher, J. Chem. Inf. Comput. Sci. 43:218-227 (2003)).

A linear array of fluid plugs suitable for conducting a crystallization screen may be chosen. For protein crystallography, arrays with different "sensitivities" can be used. That is, for a coarse screen, the array may contain plugs with different reagents. Refinement screens may contain plugs with reagents with related properties or different concentrations of the same reagent.

Markers can be used to index the linear array as described in co-pending application Ser. No. 10/765,718, incorporated herein by reference. In certain embodiments, every other plug in the linear array comprises at least one solvent and reagent, and the remaining plugs comprise at least one solvent and at least one marker.

In addition to using fluid plugs as markers, marked spacers could also be used as indexing markers. Such spacers could be colored, or could contain a component that was detectable by other means.

In other embodiments, markers may be injected at greater intervals, for example after about every 5, 25, 50, or 100 plugs. The use of markers can be combined with the use of a measuring component. Such a combination can facilitate aligning the measuring component marks with the array, and small variations of volume injected and any variations in the diameter of the receiving component would not induce significant errors (that is, the errors will not accumulate), because the measuring component can be readily realigned with the receiving component.

The holding component contains two or more fluid plugs; typically at least about 10, 20, 30, 40, 50, 60, 70, 80, 90, 100, 1000, 2000, 3000 or 10,000 fluid plugs.

The concentration of reagent in the fluid plug will depend on the goal of the reaction. For crystallization experiments, each plug in the linear array of fluid plugs typically comprises about 1 pL to 10 µL, preferably about 1 to 50 nL of plug fluid. For crystallization experiments, each plug in the linear array of fluid plugs typically comprises less than about 10 M of reagent. For some reactions, the plugs may contain reagent with a concentration less than about 1 fM. For other reactions, such as screening for nanomolar or femtomolar inhibitors for enzymes or ligands for proteins, the solutions in the plugs will be much more dilute. For applications other than crystallography, other volumes and concentrations may be used. For example, each plug in a linear array can comprise about 0.001 fL to 10 mL of plug fluid.

Combining Component

The combining component can be used (a) to merge plugs with a stream of reagent fluid, (b) to merge plugs with other plugs, (c) to form alternating plugs by injecting a stream of reagent fluid or a second set of plugs between a first set of plugs. In (a) and (b), the merged plugs may be homogenous or may be a drop-inside-a-plug or a plug-touching-a-plug. In (c), the alternating plugs may later merge, if merging is induced as described below. Additionally, a first set of plugs comprising a first fluid can be merged with a stream comprised of a second fluid that is immiscible with the carrier fluid, the first fluid and, if present, the spacer. Using this method, each plug in the resulting set of plugs will contain a section of the second fluid that divides the first fluid and is in direct contact with the two resulting sections of the first fluid.

The combining component may use active on-chip and off-chip components (such as valves, etc) to control the flow. Simple combining components that contain only or predominantly passive components would be preferred for some applications. Some of the passive combining components are described below.

In some embodiments, the combining component comprises at least one delivery microchannel, which is suitable for delivering an additional reagent to a plug without significant formation of new plugs containing just the additional reagent. In other embodiments, such as systems for free interface diffusion crystallization experiments, new plugs containing the additional reagent are formed in the combining component.

In one embodiment, the combining component may use a stream of the reagent fluid merged through at least one channel. Various methods of inducing and controlling fluid flow may be used. For example, the stream of reagent fluid may be driven by a method that generates constant pressure. The pressure may be chosen such as it is lower than the capillary pressure of the reagent stream entering the carrier fluid. If this is the case, the stream will not enter the carrier fluid and will preferentially inject into the plugs. The capillary pressure of the reagent stream may be increased by decreasing the diameter (at the junction) of the channel through which the reagent stream is applied. In addition, it may be increased by increasing the surface tension at the carrier/reagent stream interface. If the flow rate is controlled volumetrically, for example by a syringe pump, then a similar effect may be obtained by introducing an elastic element between the pump and the merging junction. Preferably, capillary pressure is sufficient to change the capacity of the elastic element by approximately the volume of the reagent stream desired to be injected into the plug. The elastic element may be, for example, a gas bubble (which would be compressed by the capillary pressure) or a flexible element of the microchannel (such as an elastomeric part allowing for expansion of the microchannel).

In certain embodiments, the combining component can be any microfluidic device which allows the array of plugs to be merged with either (1) a stream of reagent (such as a stream of protein) or (2) a stream of reagent plugs. In either case, once the array of plugs passes through the microchannel of the combining component, at least one merged plug will result. Reagent is transferred into at least one plug in an array as the array passes by a delivery channel in fluid connection with the microchannel. The merged plugs then flow through a downstream channel where they can be further manipulated, mixed, monitored, sorted, collected, etc. In other embodiments, such as systems for free interface diffusion crystallization experiments, the combining component can be any microfluidic device which allows the array of plugs from the holding component to be combined with (1) a stream of reagent (such as a stream of protein) or (2) a stream of reagent plugs in such a way that a new linear array of plugs is formed in which the original plugs from the holding component alternate with new plugs containing the introduced reagent.

Figure 4:
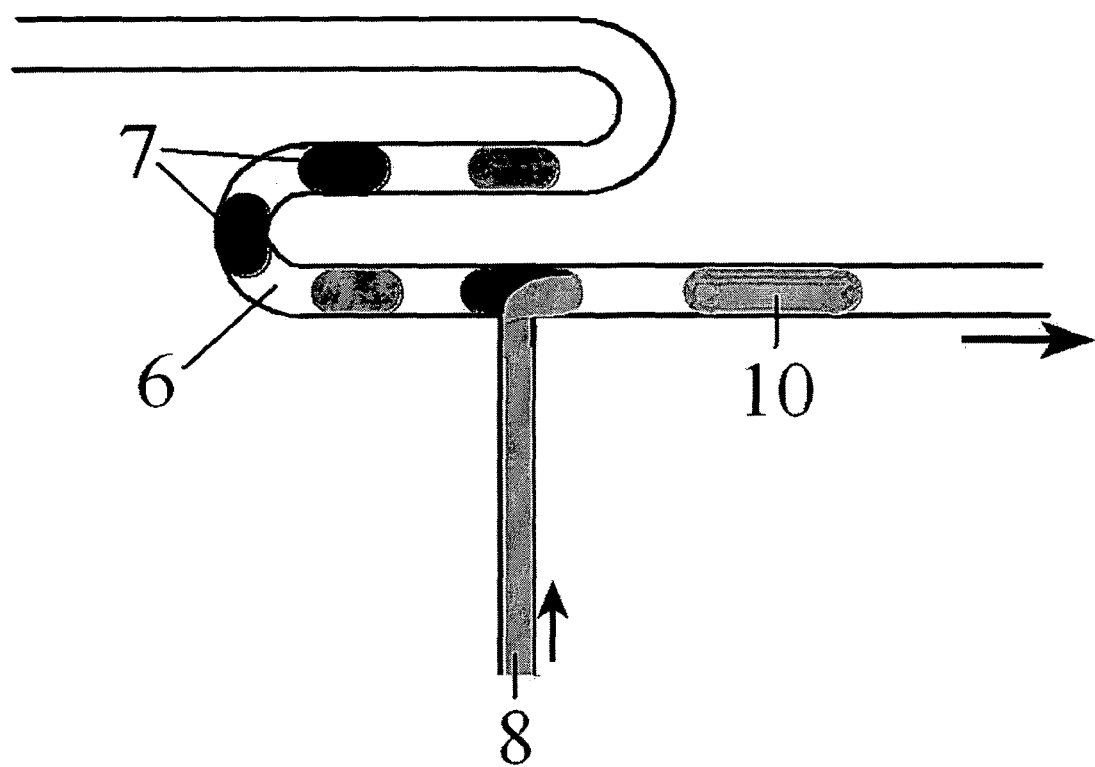
FIG. 4. Merging with split multiple microchannels. a) Three-dimensional cross-section of a microchannel showing a plug merging with a stream flowed through a split channel.

FIG. 4a illustrates a combining component comprising multiple delivery channels 22 configured to be substantially parallel in relation to each other, each delivery channel perpendicular to and in fluid communication with a microfluidic combining channel 23. The delivery channels branch from a common inlet channel 24 and due to their relatively short length act in concert. In this embodiment, an array of plugs in the holding component can be delivered to the combining component through one end of the microfluidic combining channel 23. A reagent solution (such as an aqueous protein stream) is delivered to the inlet channel 24. As plugs pass by the delivery channels, the reagent solution is delivered to the plugs. The merged plugs flow through the combining component and can be collected in a second holding component or delivered to a receiving component for further manipulation.

Channels with a narrowed junction can be used to reduce potential problems of cross-contamination of the introduced reagent stream by reagents in the array of fluid plugs during merging. For example, in protein crystallization experiments in which a protein stream is introduced to an array of fluid plugs containing a variety of precipitation reagents, it is desirable to avoid cross-contamination of one precipitant from one plug to another upstream plug via contamination of the protein stream. The use of a smaller delivery channel limits the amount of reagent that can be added to each plug, however. To enable the introduction of larger quantities of reagent, while maintaining the advantages of narrowed junctions, merging junctions can be fabricated with split multiple channels. In comparison to a single channel with an identical total cross-sectional area and volumetric flow rate, the divided channels have a significantly higher shear rate than a single wide channel, thereby reducing contamination by diffusion. The smaller channels will also act to reduce any surface tension driven convection. Such multiple small junctions can also be used to aid the selective merging process in vapor diffusion.

Channels may act in concert when the capillary pressure of the stream being delivered through a delivery channel is approximately equal to or larger than the pressure drop across the delivery channels. If a plug comes into the proximity of one of the delivery channels, and the reagent stream merges with the plug, the reagent stream will flow into the plug. The pressure due to surface tension at the carrier fluid/merging stream interface will resist the flow of the reagent into the carrier fluid through other delivery? channels. For example, if three delivery channels are used, and the reagent stream is flowing only through one of the channels, the pressure due to surface tension at the carrier fluid/merging stream interface at the other two channels should be sufficiently high to be able to sustain the pressure equal to the pressure drop due to the flow of the reagent fluid through the one channel. The pressure due to surface tension at the carrier fluid/merging stream interface depends on the geometry of the junction between the delivery channels and the combining channel. The pressure drop depends on the length of the delivery channels, their cross-sectional dimensions, the viscosity of the reagent fluid, and the flow rate. Therefore, many parameters may be adjusted to achieve the desired relationship between the pressure due to surface tension at the carrier fluid/merging stream interface and the pressure drop.

Multiple delivery channels and the spacing between the plugs may be designed such that there is always at least one plug in the vicinity of a delivery channel. This configuration enables consistent merging of the stream with plugs, without the injection of the reagent stream into the carrier fluid. In addition, such a configuration may be used to achieve selective merging, where only some of the plugs merge with the reagent stream, for example only the first type of plugs merges with the stream, while the second type does not. Selective merging may be achieved when the second type of plugs have a lower tendency to merge with the stream of reagent (this selectivity may be achieved, for example, by increasing the viscosity of the second type of plug fluids, or by decreasing the surface tension at the second plug fluid/carrier interface). In addition, polymers may be added to the second plug fluids, especially surface active polymers that would increase interfacial viscosity. To achieve selective merging, this configuration may be used especially when the delivery channels and the spacing between the plugs is such that there is always at least one plug of the first type in the vicinity of the delivery channel.

FIG. 12 shows an example of another possible merging geometry that is also designed to minimize cross-contamination. In this geometry, a small side channel is used to direct the carrier fluid to assist to break off the reagent stream.

In some applications, it may be preferable to drive the flows into the combining component using a simple method, for instance one that is not capable of providing substantially constant pressure or constant volume flow to one or more inlets. Some methods may be designed so they do not require electric power or computer control. Such methods would be useful for in-the-field diagnostics and testing, and for other applications where simplicity and low cost are desirable. For example, in the combining component, the relative flow rates of the plugs through the holding component and the stream of reagents to be combined must be controlled. This control may be easily achieved with multiple syringe pumps or other established methods of pumping. In addition, one may use a fluidic rationing device. This device would be placed in between a pressure source, such as a syringe or a pump, and the fluid streams or arrays to be pushed. This device may be designed as a Y-junction, with the inlet corresponding to the bottom of the Y, and the two outlets corresponding to the top of the Y. The device may be filled with a carrier fluid or carrier fluids, and the outlets connected to the inlet of the holding component and the inlet corresponding to the reagent stream of the combining component. The ratio of fluidic resistances of the two outlets may be configured to correspond to the desired ratio of flow rates. The individual fluidic resistances of the two outlets could be controlled by individually varying the relative lengths and/or diameters of the two arms of the Y. Preferably the fluidic resistance of the two outlets of the Y are significantly higher (for example by a factor of 100) than the fluidic resistances of the holding and combining components, so that the flow rates through the holding and combining components are determined by the ratio of fluidic resistances of the two Y outlets. An analogous approach may be used to control flow rates of more than two streams. This approach is attractive because, in many applications, as long as the capillary number is in the correct range, the plug behavior is determined by the ratio of flow rates, rather than the absolute values of flow rates. In this approach the flow may be driven by a single pump or by hand, and still provide the correct ratios of multiple flow rates. Such a fluidic rationing device could be offered in a kit with a holding component.

Any volume of reagent solution can be merged with a fluid plug. The flow rate of the reagent solution can be varied during combining to vary the concentration of reagent in the merged plugs. The amount of reagent delivered is essentially determined by the intended detection technology. For example, femtoliter amounts (or less) of reagent solution can be delivered if the reaction product can be detected.

For protein crystallization, typically the volume of protein solution to be combined with the plug fluid is similar to the volume of the plug fluid (typically a 1:5 to 5:1 ratio of protein solution to plug fluid is used). The amount of the protein solution combined with the plug can be controlled by the ratio of the flow rates of the plug stream and the protein stream. Again, the amount of protein solution delivered will depend on the goal of the experiments. If the goal is simply to detect the formation of crystals or precipitates, pL volumes can be used. If the goal is to obtain a crystal structure, 10 nL or more may be necessary. In general, about 1-100 nL, preferably about 10 nL, of protein solution is delivered to each plug. For protein crystallography, typically the concentration of protein solution is about 0.01 to 100 mg/mL, preferably 0.1 to 50 mg/mL.

Receiving Component

The receiving component comprises a first microchannel with at least one open end configured for making a fluid connection with a combining component or other microchannel. The receiving component can be a microfluidic device such as that described elsewhere in this application. The receiving component can be constructed identically to the holding component described above. When used to conduct protein crystallography experiments, it may be useful for the receiving component to be constructed of a material, such as glass, suitable for on-component x-ray diffraction of crystals formed in plugs. When used for assays, the receiving component may be constructed of a material suitable for optical detection such as glass or plastic.

The receiving component can comprise a device to control the temperature of the contents of the plugs, for example, in order to control the rate of reactions. The receiving component could also comprise a device for illuminating or irradiating the contents of the plugs, for example to initiate photochemical reactions. The receiving component can be designed to sort or monitor plugs. The receiving component may be separate from or integrated with devices for detecting or analyzing the contents of the plugs.

The receiving component may comprise an active surface. This active surface may induce wetting by the plug fluids. Wetting by plug fluids may be used, for example, to create contact between plug fluids, for example in macromolecular crystallization by free-interface diffusion. This active surface may also be reactive. The reactions may occur upon contact with plug fluids, and/or by transfer of the reagents between the plug fluid and the surface (in either or both directions) through the carrier fluid, spacers, or markers.

Measuring Component

The measuring component allows the user to identify individual plugs by their location within the microchannel. A measuring component may be useful if the number of plugs in a linear array is too large to allow manual counting of the plugs. It may also be useful if automated counting of plugs is desired.

The receiving component can comprise an integrated measuring component (such as one or more physical marks) for identifying the placement of a fluid plug within the microchannel. Alternatively, a measuring component separate from the receiving component can be used. When a separate measuring component is used, it is preferable to provide a kit containing the measuring device and the receiving component. In certain embodiments, a kit can comprise a holding component and a matched measuring component designed to indicate the location or locations of the contents of the holding component after they have been moved to the receiving component. The measuring component could, for example, be a card designed to fit onto a receiving component.

The measuring component can be a ruler, where the measurement markings correlate to the location of plugs within an array in a receiving component. The measurement markings can be formed by dots, lines, segments, etc. The markings can be luminescent (fluorescent, phosphorescent, chemiluminescent, etc), reflective or absorbent, based on differences of refractive index, and other form of optical marks. Markings can also be magnetic, charged, topographic, etc.

The markings could be numbers as well. The markings can be human-readable, and could include words, or can be machine-readable, or both. Possible machine-readable markings include barcodes, implemented, for example, using any of the methods above, and also including nanoscale barcodes as described in Nicewarner-Peña, et al., Science 294: 137-141 (2001).

The measuring component can aid visualization when the plugs are difficult to locate visually, as may occur when the carrier and plug fluids have matched refractive indices. Refractive index matching can be helpful for visualizing the contents of plugs.

A measuring component need not mark the location of every plug. It could simply mark multiples of plugs, e.g. every third plug or every fifth plug, or could mark the location or locations of significant changes in reagent composition along the linear array of plugs.

To aid the user, the array of plugs could contain marker plugs or spacers. The marker plugs or spacers could then be used to allow the user to initially align the measuring component with the array, or to help the user identify the plugs in the receiving component without the use of the measuring component. Several types of markers may be used. For example, a marker of the first type every tenth plug, a marker of the second type every fiftieth plug, and a marker of the third type every $250^{th}$ plug, etc. The different types of markers can differ, for example, by color.

Formation of Components

Components comprise microchannels that can be formed using methods known in the art. For example, pending application Ser. No. 10/765,718 describes the manufacture of microchannels and use thereof for splitting, merging, and otherwise manipulating fluid plugs.

Components of this invention can be formed from capillaries, tubing with a diameter of less than about 10 mm, preferably less than about 1 mm, substrates with etched, or molded, or embossed microchannels, or combinations thereof. Components may contain multiple channels, either joined together or separated. Preferably, the microchannels have a circular or rounded cross section, rather than a rectangular cross section, to facilitate transport of plugs and reduce coalescence of plugs. However, any shape can be used.

To fabricate channels with circular or nearly-circular cross-section, thin pieces of tubing or capillaries may be inserted into rectangular channels. This technique may facilitate formation of plugs, and also may provide a method of connecting chips with other components. Multiple pieces of tubing may be inserted into multiple channels. The tubing or capillaries may be chosen such that they are preferentially wetted by the carrier fluid. For example, Teflon is preferentially wetted by fluorinated fluids over aqueous fluids. The tubing or capillaries may optionally have flared, funnel-like ends (or narrowed ends) to facilitate connections with other components. To fabricate such devices, the tubing or capillary may be either inserted into the channel before sealing of the layers (such as the sealing of PDMS layers), or after the rectangular channel is fabricated. It may also be desirable to fill the space between the outer surface of the tubing or capillary and the rectangular channels. This space may be filled with a viscous liquid, or a polymer. PDMS may be used, for example.

Individual components can be formed from the same or different materials. Components can be formed from a material that responds to contact with water. Polymers have been synthesized that respond to contact with water (Senshu et al., Langmuir, 15, 1754-1762 (1999); Mori et al., Macromolecules 27, 4093-4100 (1994)). These diblock polymers contain hydrophilic and hydrophobic domains. When exposed to air, the hydrophobic block migrates to the surface to minimize the surface energy and the surface is hydrophobic. Upon contact with water, surface reconstruction occurs and the hydrophilic block migrates to the polymer-water interface until the water is only in contact with the hydrophilic block. Exemplary polymers include poly(styrene-b-2,3-dehydroxypropyl methacrylate) and poly(4-octylstyrene-b-2,3-dehydroxypropyl methacrylate).

Opaque particles such as carbon black particles (preferably those with diameters smaller than about 5 microns) can be incorporated into the material used to make the components. In this manner, substantially black channels can be fabricated, eliminating the problems associated with background light (e.g. increasing the sensitivity of fluorescent analysis).

An adapter may be used as a connection, for example to connect capillaries or pieces of tubing. The adapter may be a short piece of glass tubing with the I.D. (inner diameter) narrowing in the middle. Adapters of different I.D's are commercially available. The surface chemistry of the inside wall of glass adapters can be made hydrophobic by silanization. Adapters can also be fabricated easily from stretched Teflon tubing. To do this, a piece of Teflon tubing is stretched at a point. Both the I.D. and O.D. (outer diameter) of the stretched point will decrease resulting in tubing suitable for the use as an adapter.

Plug Formation

As used herein, "plugs" are formed when at least one plug-fluid is introduced into the flow of a carrier in which the plug fluid is immiscible. The flow of the fluids in the microfluidics device is induced by a driving force or stimulus that arises, directly or indirectly, from the presence or application of, for example, pressure, radiation, heat, vibration, sound waves, an electric field, or a magnetic field. Plugs may vary in size but, when formed, their cross-section is typically similar to the cross-section of the channels in which they are formed. In non-circular shaped channels, the plugs should be similar in cross sectional size to the cross section of at least one-dimension of the channel. The plugs should be substantially surrounded by carrier. That is, the carrier fluid should wet the microchannel to a greater extent than does the plug fluid. The cross-section of a plug may change if it passes into downstream channels of differing diameter or when it is merged with additional fluid. Plugs may vary in shape. The term "plugs" also includes plugs-within-plugs, drops-within-plugs and solids (such as beads)-within-plugs. An exception to this general definition is that a plug can be smaller than the cross section of a microchannel when spacers are used.

"Merged plug" as used herein refers to either (1) the combination of two or more plugs to form a single plug or (2) the juxtaposition of two plugs in a microchannel so that they will merge with time.

In order to form and move plugs through a microchannel with minimal dispersion, the fluid inside the plugs must not adhere to the walls of the microchannel. To achieve this, the surface tension at the plug/channel interface must be higher than the surface tension at the plug/carrier interface. When the plugs are aqueous and the carrier is an oil, the dimensionless capillary number Ca is ideally less than about 0.1:

$$Ca=U\mu/\gamma$$

wherein, $\gamma$ [N m−1] is the surface tension at the oil/water interface, U is velocity in m/sec and $\mu$ is viscosity (Pa·sec).

The microchannels used in the present invention can be surface treated to make them wettable by the carrier fluid preferentially over wetting by the plug fluid. For example, a glass capillary can be silanized to decrease the wetting of aqueous plugs versus a carrier. In addition, a microchannel can be initially flushed with carrier prior to introduction of plugs.

Plugs can be formed from essentially any fluid such as from one or more aqueous solutions, one or more organic solutions, one or more inorganic solutions, or mixtures thereof. Plugs can be formed from water, stock solutions, buffers, reagents, solvents, salt solutions, polymer solutions, precipitant solutions, metal suspensions, cell suspensions, or the like.

The size of the plug can be controlled as described throughout this application; for example, by the relative volumetric flow rates of the plug fluid and carrier into the microchannel. Volumetric flow rates are preferably controlled using pumps.

Various processes may occur during formation of plugs. For example, formation of lipidic cubic phases (LCP) may occur when a stream of a lipid (such as MO, monoolein) is combined into a plug with an aqueous solution, and the two liquids are vigorously mixed inside a plug. An aqueous solution of a macromolecule, such as a protein or a membrane protein, may be used. This mixing may be performed by chaotic advection, induced when a plug is traveling through a plurality of bends in a winding channel (as previously described by the present inventors). Viscous carrier fluid may be used to induce higher shear inside the plugs, to ensure more effective mixing. This method is attractive, for example, for miniaturizing crystallization in LCP.

The spacing between plugs in microchannels can be controlled in a number of ways. In one embodiment, one set of reagent solutions is continuously injected into a flow of immiscible carrier fluid to form plugs and a second set is continuously injected further downstream. If carrier fluid with suitable surfactant is used, the second set of solutions will prefer to form plugs that are dispensed directly adjacent to plugs that are already formed, rather than to inject into them. The plugs are kept from coalescing by surfactant assemblies at the interfaces between the reagent solutions and the carrier fluid, and by a layer of the carrier fluid between the two plug fluids. Pairing up of plugs in the main channel would occur if plug fluids have different properties, for example different viscosities. This pairing up may be useful for applications, for example for crystallization of macromolecules using vapor diffusion and in free-interface diffusion methods.

Plugs of alternating composition can be formed by flowing aqueous solutions head-on into a stream of carrier. The flowing carrier provides a barrier between the plugs that prevent them from coalescing. Formation of alternating plugs is controlled by the capillary number. For microchannel inlets of the same width, the ratio of the flow rate of the aqueous streams will determine the ratio of the size of the droplets. If the flow rate of the top aqueous stream is two times faster than the flow rate of the bottom aqueous stream, then the size of the resulting droplets will then be in an approximately 2:1 ratio. In some cases, plugs of approximately the same sizes may form, but two plugs from the faster stream may form for every one plug of the slower stream. The ratio of the dimension of the microchannel inlets can also be designed to affect the size ratio of the droplets. If the microchannel for the top aqueous stream is two times wider than the microchannel for the bottom aqueous stream, then the size of the resulting droplets may be in an approximately 2:1 ratio. Pairing up of alternating plugs in the main channel would occur if plug fluids have different properties, for example different viscosities.

The concentrations of solutions of the plugs along the array can be rapidly varied simply by changing the relative flow rates of the plug fluid stream components. This principle can be used to set up linear arrays of plugs in a microchannel. For example, it can be used to set up crystallization trials by forming varying concentrations of protein and/or varying concentrations of precipitating agent within an array of aqueous plugs. Preloaded cartridges containing such linear arrays can be used for optimization of crystallization conditions.

In some embodiments it may be simpler or less expensive to form plugs larger than the plugs required for an application. For example, it may be straightforward to make reliably larger plugs of about 1 microliter in volume, rather than smaller 10 nL plugs desirable for protein crystallization screening. If a loading component is available for controlling larger volumes of fluid, it may be preferable to connect multiple holding components to one loading component, and fabricate in parallel multiple holding components with smaller plugs. For example, if a robotic loading component is available to aspirate 1 microliter volumes, and 25 capillaries are connected in parallel to this loading component so that equal volumes are aspirated into each capillary, then by successfully aspirating 1 microliter volumes of plug fluids, carrier fluids, and spacers, an array of capillaries would be created that would contain smaller approximately 40 nL plugs, separated by approximately 40 nL of carrier fluid and approximately 40 nL spacers. The robotic loading component could, for example, aspirate in sequence carrier fluid, a spacer (air, for example), carrier fluid, a first reagent composition, carrier fluid, a spacer, carrier fluid, a second reagent composition, carrier fluid, a spacer, carrier fluid, a third reagent composition, carrier fluid, etc. The capillary pressure for the solution entering the holding components is preferably significantly lower than the pressure (or pressure differential) used to drive the flow. This would ensure that the fluids are entering all holding components to a substantially equal extent. In addition, the entrance into the holding component may be designed so that there is an increase of the capillary pressure as plug fluids enter and proceed into the holding component (in one embodiment, this increase may be achieved by using a holding component that narrows from the point of entrance). Such an entrance may facilitate more equal distribution of volumes entering the holding component. Preferably, the holding components are not wetted by the plug fluid, to prevent plug fluids adhering to the holding components and causing cross-contamination.

This approach described above is not limited to aspiration into multiple holding components, and is also useful for other methods of dispensing.

Plugs can also be made by splitting larger plugs into smaller ones. In this embodiment, a microchannel is split into one or more smaller receiving microchannels at a single junction. The junction is fabricated to be narrow such that the capillary number is increased. The process of splitting plugs can be controlled by adjusting the pressures or pressure drops in the receiving channels. The receiving channels are preferably designed such that the pressures due to surface tension at the outlets are significantly lower (e.g. 10 times, preferably 100 times or 1000 times or more) than the pressure drops across the receiving channels. This ensures that splitting is controlled by the pressure drops across the channels rather than by the fluids that are being dispelled at the outlets. The capillary pressure at the outlets may be reduced by pre-filling the holding component with the carrier fluid, and immersing the outlet of the holding component into a reservoir with a fluid that has low surface tension with the carrier fluids, the plug fluids, and the spacers. Also, the capillary pressure at the splitting junctions is preferably significantly lower than the pressure drops across the receiving channels. Also, the capillary number at the splitting junction should be high enough to allow for splitting to occur.

Alternatively, a long plug could be flowed into a stream of carrier fluid at a junction. The long plug breaks up into a series of smaller plugs separated by the carrier fluid.

Large plugs can be broken up into smaller plugs such that the smaller plugs contain different concentrations of the solution originally contained in the large plugs. When applied to protein crystallization, this method allows one to perform a sparse matrix screen and a gradient screen with the same array. In one embodiment, a holding component contains large (e.g., about 100 nL) plugs of the appropriate solutions for a sparse matrix screen. These large, long plugs are flowed into a stream of carrier fluid such that they break up into a series of smaller, shorter plugs. The flow rate of the large plugs relative to the flow rate of the carrier fluid controls the size of the smaller plugs. Protein solution is subsequently combined with the smaller plugs through a peripheral channel downstream, and the flow rate of this peripheral stream relative to the flow rate of the stream containing plugs controls the concentration of protein in the smaller plugs. A buffer solution may be similarly added to the small plugs to insure that each crystallization assay is performed at an identical volume. Spacers (e.g., gas bubbles) may be contained in the holding component between large plugs, and may be introduced additionally during the manipulations of plugs.

Alternatively, the large plugs may be flowed into an aqueous stream. This stream may contain one or more solutions. When applied to protein crystallization, the stream may contain a laminar flow of protein and buffer solutions. The resulting multi-component stream is flowed into a stream of carrier fluid where the combined aqueous stream breaks up into a series of plugs. Again, in this application, the large droplets may contain the solutions for a sparse matrix screen and the flow rates of the aqueous streams and large plugs may be varied to create concentration gradients of any of these reagents, resulting in a hybrid screen. Spacers may be used in the holding component between large plugs. Markers may be also used between large plugs.

Carrier Fluid

The carrier can be any liquid or gas that is substantially immiscible with the plug fluid. Preferably, when the plug is aqueous, the carrier is liquid. The surface tension of a plug fluid in a carrier is ideally between about 5-15 mN/m, preferably about 10 mN/m. Other non-zero values of the surface tension may be used. The carrier can be permeable to the plug fluid or reagents.

For membrane protein crytallography, perfluoroamines or their mixtures are ideal carriers, because they preferentially wet surfaces (especially fluorinated surfaces in Teflon devices) over the aqueous plug.

In some embodiments, it is desirable add a surfactant into the carrier fluid. Surfactant may be used to control the surface tension and the wetting properties of the carrier fluid. We have used 1H,1H,2H,2H-perfluorooctanol as the surfactant when fluorinated fluids were used as carrier fluids. Surfactants may also be used to control non-specific adsorption of the contents of the plug to the interface between the plug and the carrier. For example, fluorous-soluble surfactants can be used to control non-specific protein adsorption at a fluorinated carrier-aqueous interface. An exemplary fluorous soluble surfactant is the oligoethylene glycol molecule triethyleneglycol mono [1H,1H-perfluorooctyl]ether $CF_3(CF_2)_7CH_2O(CH_2CH_2O)_3H$). This surfactant arranges itself at the fluorinated carrier-aqueous interface during plug formation and presents a monolayer of oligoethylene glycol groups. This interface resisted the adsorption of a wide variety of proteins and enzymes, including a concentrated solution of fibrinogen, a protein known to adsorb quickly and strongly to surfaces. Surfactants with the same ability to resist non-specific adsorption can be extracted from commercially available Zonyl FSO-100 from DuPont via fluorous-aqueous extraction. Other oligoethylene glycol congeners with variable fluorinated alkane chain lengths, variable glycol lengths, and various spacer links also prevent protein adsorption at the aqueous-fluorous interface. Conversely, surfactants capped with non-inert functional groups can attract and bind proteins to the liquid-liquid interface.

Spacers

The arrays of the present invention can optionally contain spacers. Suitable spacers are composed of at least one liquid (e.g., ionic liquids, fluorosilicones, hydrocarbons, and fluorinated liquids), gas (preferably an inert gas such as nitrogen, argon or xenon), gel or solid (e.g., polymers such as polystyrene) that is immiscible with both the plug fluid and the carrier. The arrays of the present invention can contain multiple types of spacers.

Spacers can also contain markers so they can be used to index plugs as described above. Spacers may also be used to reduce cross communication (e.g. by preventing optical communication or by preventing permeability) between plugs. Spacers may also have functional properties—for example, when xenon bubbles are use as spacers in macromolecular crystallography, especially when experiments are conducted under increased pressure, xenon may incorporate into a growing macromolecular crystal, improving its diffraction properties.

The spacer can be formed and manipulated using the similar methods described for formation and manipulation (e.g. splitting) of plugs composed of a liquid. In particular, a stream composed of both liquid plugs and gas bubbles may be formed using the same methods used to form streams of plugs of alternating liquid compositions. Spacers may be introduced during the robotic fabrication of the array. If an array of larger plugs separated by spacers, is split to fabricate several array of smaller plugs, then spacers are preferably also split.

Spacers can play an important role in manipulations of plugs. First, if undesirable merging of plugs occurs, spacers can be inserted between the plugs to minimize merging. Such spacers may allow transport of an array of plugs through longer distances than without the spacers. Such spacers may also facilitate transfer of plugs in and out of devices and capillaries (or transfer through composite devices made of combinations of devices and capillaries).

Spacers may also be used to facilitate free interface diffusion inside a plastic or PDMS channel. With a gas bubble in between plugs containing reaction components, by applying pressure from both ends, the gas bubble is purged out through the plastic or PDMS wall. The two plugs are then brought close enough to allow diffusion across the newly formed plug-plug interface. Such a system may be applied to protein crystallization, where one plug contains protein and the other contains precipitating agent. If pressure is applied, and the gas bubble is compressed, the plugs separated by the spacer may come into contact.

Kits

As discussed above, one embodiment of a kit comprises a receiving component and a measuring component.

In another embodiment, a kit of the present invention can comprise a combining component, a reservoir and a pump. A pump suitable for use in this embodiment is one which can provide sufficient pressure to drive a solution, for example, a protein solution, from the reservoir through the inlet, through the delivery channels, and into the microchannel of the combining component.

In another embodiment, a kit comprises 2 or more holding components. For example, the holding components in the kit could span a portion of chemical space. In another embodiment, the kit could comprise multiple holding components spanning a genome.

In another embodiment, a kit comprises a combining component and one or more receiving components, wherein the microchannels of the combining and receiving components are sized and shaped so that they can form a fluid connection with each other. The kit can also contain two, three, four, five, ten, twenty, fifty or more receiving components.

In another embodiment, a kit comprises one or more holding components and a combining component, wherein the microchannels of the combining and holding components are sized and shaped so that they can form a fluid connection with each other.

In another embodiment, a kit comprises one or more holding components, one or more combining components, and one or more receiving components, wherein the microchannels of the combining, holding and receiving components are sized and shaped so that they can form a fluid connection with each other.

In another embodiment, a kit comprises one or more loading components, one or more holding components, one or more combining components, and one or more receiving components, wherein the microchannels of the loading, combining, holding and receiving components are sized and shaped so that they can form a fluid connection with each other.

Transfer of an Array of Plugs into Various Components

The plugs can be transferred from one component into another by inserting one end of a component directly into one end of the other component and sealing the junction to inhibit leaking. Alternatively, an adapter (such as a funnel) can be used to connect the various components.

The plugs may be pushed from the microchannel of a first component into the microchannel of a second component by applying a pressure to the end opposite the outlet of the first component or may be pulled into the second component by applying a vacuum inside the channel of the second component. Other standard methods of driving fluid flow can also be used as described above.

The rate of mixing of various fluids in a plug can be controlled as described in copending application Ser. No. 10/765,718. For example, when plugs are transported through winding channels, rapid mixing can be induced. To increase the reaction time in plugs that are transferred from the loading component into the holding component or from the holding component to the combining component, or from the combining component to the receiving component, they may be either transported through at a sufficiently low velocity, or with flow completely stopped or significantly reduced.

In some applications of the present invention, it is desirable to allow a plug to be combined with more than one subsequent plug or stream, either in immediate sequence or with some delay between the combining events. In some embodiments, the combining component can contain more than one delivery channels connected to a corresponding number of reservoirs, allowing an array of plugs to pass by the delivery channels sequentially. Reagent from each delivery channel is thus transferred into each plug as it passes by each inlet. In such an embodiment, delay between each transfer of reagents can be controlled by the distance between the delivery channels and the flow rate of the array of plugs. In other embodiments, a receiving component containing an array of plugs previously combined with a first reagent using a combining component can be subsequently combined with a second reagent using a combining component. The combining component used in combining with the first reagent may be either the same device or a different device than that used in combining with the second reagent. For example, an array of plugs containing a library of small molecules which are potential inhibitors of an enzyme can be first combined with an enzyme solution and allowed to equilibrate. Subsequently, this array of plugs containing enzyme and small molecules can be combined with the enzyme's substrate, and the enzyme-catalyzed reaction can be monitored to determine the efficacy of the potential inhibitors. The use of tubing with approximately circular cross-section is especially useful for achieving reliable transport of plugs over long distances, and it may be also employed to achieve appropriately long delays for reactions.

Components can be reused. For example, the outlet of a loading component can be connected to a first holding component (such as a capillary) to collect an array of plugs. After transfer of the array, the first holding component can be taken off the loading component and, if necessary, sealed or capped. A second holding component can then be connected to the loading component and filled. Combining components may be reused in a similar fashion.

Automated devices can be used to interface multiple loading and holding and receiving components. For example, one loading component may be used to load plugs into many holding components, which are switched into place by an automated piece of equipment. During incubation, the holding or receiving components may be transported to a monitoring station that would monitor the extent of reaction or crystallization in plugs. The holding or receiving components may be continuously transported past the monitoring station or several stations. This monitoring could be used, for example, to detect a plug or a series of plugs in which crystallizations or reactions took place. The receiving component could be used, for example, to detect, sort and/or separate plugs in which desired processes took place.

Figure 1:
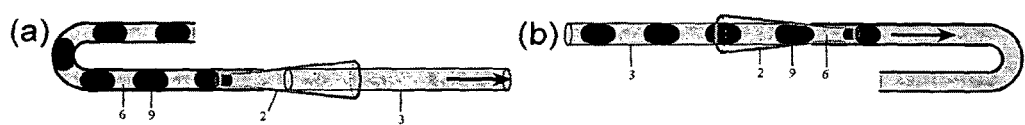
FIG. 1. A schematic illustration of a design of a reusable microfluidic system. The plugs 9 in a carrier 6 can be transported either (a) from a microchannel in a microfluidic device to a capillary 3 or (b) from a capillary to a microchannel on a microfluidic device via an adapter 2.

FIG. 1 illustrates a funnel shaped adapter 2 that can be used to make a connection between holding and loading components. In this illustration, the holding component is a capillary 3 and the loading component is a microfluidic device 1. Alternatively, the adapter can be attached either to the microfluidic device or the capillary.

Figure 2:
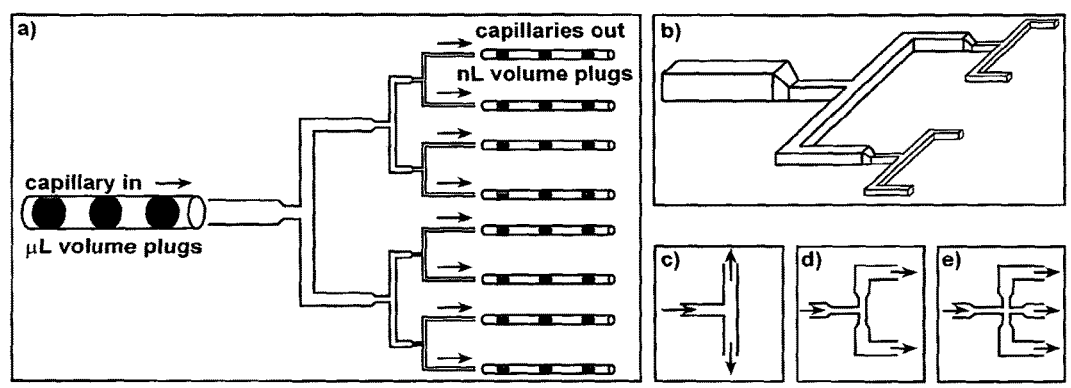
FIG. 2. Mass-producing holding components containing plugs. a) Device Schematic. A large channel containing a series of different plugs separated by carrier is fed into a splitting component. Each junction splits each plug into two separate plugs. After three iterations, 8 small holding components are each filled with an identical series of plugs. b) 3-dimensional view of splitting channels. Since all iterations rest on a common plane, successive layers can be built up using multilayer photolithography. c) a simple T-junction. d) Narrowed junctions. e) Junctions with multiple outlets.

FIG. 2a illustrates how a single array of larger plugs can be split into multiple arrays of substantially identical character, each containing smaller plugs. This splitting is achieved by continuous directing the initial fluid flow into pairs of smaller sized channels of substantially similar sizes. Such a device can be used to split arrays of microliter-size plugs in a microfluidic device with large (for example, ~800 µm) channels into nL plugs in smaller channels.

Reactions within Plugs

The present invention provides a system for plug-based microfluidic manipulation of small volumes of solutions. The system contains a loading component, a detachable holding component, a combining component and a receiving component.

Reactions can take place within plugs in any of these components. Reactions may also take place involving the surfaces of these components. The components may be placed into conditions (such as temperature, irradiation with light and other forms of radiation, exposure to various fields, etc) that maximize the desirable reactions. For example, if ligands and metal ions are loaded into the plugs of the component, the formation of the ligand-metal complexes may proceed inside the plugs. The components may be placed under conditions to minimize the undesirable reactions. For example, when aqueous solutions of biomolecules and/or organic molecules are in plugs, undesirable hydrolysis may take place. This hydrolysis may be minimized by controlling the temperature of the component, and also by freezing the plugs inside the component. Photobleaching of reagents inside the plugs inside the component may be minimized by minimizing the exposure of the plugs to light, either by using components that are substantially not transparent to light, or by minimizing the exposure of the component to light. If reactions of reagents inside the plugs with oxygen are undesirable, then the component may be fabricated with gas-impermeable materials such as glass, or the component may be maintained under oxygen-free atmosphere. In addition, the carrier fluid (such as a fluorinated fluid) may be degassed (for example, by freeze-pump-thaw cycles or by bubbling with an inert gas such as argon) to remove any dissolved oxygen.

The types of reactions which can be conducted within plugs are not limited. Examples include, but are not limited to, protein crystallization, synthetic reactions, screening and enzymatic reactions, and diagnostic assays. Throughout this disclosure the use of the present invention is exemplified by application to protein crystallography. It should be understood that this invention is equally applicable to other reactions.

Plug-based microfluidic manipulation of solutions has been described previously by the present inventors in U.S. Ser. Nos. 10/434,970 and 10/765,718, incorporated herein in their entirety by reference.

The present invention also provides a method for conducting reactions in plugs. The method comprises (a) introducing from a holding component a linear array of plugs of first plug fluid separated from each other by a first carrier and/or spacer into a first microchannel within a combining component with a first flow rate; (b) introducing either (i) a stream of second plug fluid or (ii) a stream of plugs of a second plug fluid separated from each other by a second carrier into a second microchannel within the combining component with a second flow rate; and (c) merging at least one plug of first plug fluid with at least some second plug fluid to form a merged plug, wherein said merging occurs at a junction in fluid communication with the first and second microchannels.

In another embodiment, the linear array of reagent plugs is introduced into the microchannel by attaching a holding component within which is disposed a linear array of reagent plugs. Because the reagent plugs can be stored in the holding component for long periods without loss of integrity, the array of plugs can contain active nucleation particles (such as aggregates of protein molecules or simply nanoparticles). The reagent plugs can be stored and/or transported, and used later to induce nucleation for the crystallization or precipitation of proteins or other molecules or materials. For example, the researcher could purchase a holding component containing an array of reagent plugs for a protein crystallization screen, and then use a simple junction, and a simple source of flow (such as a syringe or pressure) to merge the array of merged plugs with a stream of reagent or a stream of plugs.

For some applications, a plurality of different holding components may be used together. For example, a capillary (a first holding component) containing 96 precipitants for protein crystallization in plugs may be prepared using a loading component. Separately, a second holding component (for example, another capillary) may be prepared with plugs containing a protein to be crystallized. In this example, a crystallization experiment is carried out by merging the plugs of the protein sample with the plugs of the precipitant (using techniques described elsewhere in this application, or in co-pending application Ser. Nos. 10/434,970 or 10/765,718). For example, the first and second holding components may be connected by a T-junction and their contents forced into a third holding component.

The components containing the merged plugs can also be subjected to one or more of light, an electric field, a magnetic field, heat, radiation, etc. to conduct reactions (including protein crystallization) and various studies on the merged plugs. For example, nucleation of protein crystals may be induced in this way. For example, a component containing the merged plugs can be subject to a temperature gradient to understand the effect of temperature on the reaction. Ultimately, by tracking the reaction and by manipulating temperature, active control of the reaction can be achieved.

Plugs can be sorted. For example, the plugs can also be sorted according to their sizes. Alternately, the plugs can be sorted by their density relative to that of the carrier fluid. Alternately, plugs can also be sorted by applying a magnetic field if one group of the plugs contains magnetic materials such as iron or cobalt nanoparticles or ferrofluid.

Reactions in plugs can be monitored in any of the components of the microfluidic system or can be monitored after exiting the components of the microfluidic system. Plugs can be monitored using a variety of techniques including fluorescence polarization, fluorescence perturbation, fluorescence correlation spectroscopy, mass spectroscopy, etc. For example, crystals can be removed from the microfluidic system and analyzed with x-ray diffraction. Plugs can be removed from the microfluidic system and analyzed with mass spectroscopy.

Control of the Distance Between Plugs

The distance separating two plugs can be controlled with flow if the carrier is chosen properly. In FIG. 5c, flow is applied to the channel such that the plugs remain separated. In FIG. 5d, no flow occurs through the channel; if the carrier is chosen properly, the distance between plugs will decrease and ultimately the plugs will merge, if allowed.

The distance of two plugs can be decreased in a number of ways. For example, a channel whose diameter increases along its length can be used. The distance between plugs would decrease if the plugs are moved towards the widening of the channel. In some cases, merger can also be promoted by increasing the diameter of the microchannel as the plugs will eventually merge as they move through such a channel. In some cases, obstacles, expansions or constrictions can be introduced to change the velocity of the plugs and also to control merging.

Another way to decrease the distance of two plugs is to gradually remove the fluid between two plugs. For example, two plugs separated by a gas bubble can be moved closer together by applying pressure on either side of the plugs. If the wall of the microchannel is permeable to gas, the gas can be purged out. The two plugs then get closer to one other and eventually merge. If the wall is not permeable, as in the case of a glass capillary, the gas is compressed and the volume decreased, therefore, the distance between the two plugs may be still decrease, but merger would be prohibited.

FIG. 7 shows a means for changing the distance between plugs. When the pressure in the microchannel is higher than the pressure in the side branch channel, the carrier is removed and the distance between plugs decreases (and eventually merges). When the pressure in the side branch channel is higher than the pressure in the microchannel, then carrier is added and the distance between plugs increases. Carrier can be replaced using this design by having one side branch channel removing carrier, and another side branch channel adding another carrier.

If further manipulations are required (further reactions, treatment, merging and/or sorting, for example) the merged plugs could be transported to another holding component or a receiving component.

Crystallization of Biological Macromolecules

Microbatch and vapor diffusion are the two basic crystallization methods for the plug-based microfluidic system. Pending U.S. application Ser. No. 10/765,718 describes these techniques in a plug-based microfluidics system, and is herein incorporated by reference.

Using the present invention, plugs containing solutions for crystallization can be loaded into a holding component using a loading component. After using a combining component to add a solution of the macromolecule of interest, crystallization trials can then be conducted in the receiving component when flow is stopped. The present invention is capable of handling solutions having a wide variety of surface tensions, viscosities, and wetting behaviors. Additionally, it allows minimally invasive evaluation of crystal quality by diffraction while in the receiving component, thus avoiding damage of fragile crystals by handling. In addition, crystals can be removed from the receiving component. The receiving component may be cut or otherwise disassembled to allow for the removal of crystals, or crystals may be flowed out of the intact receiving component. Removal of crystals may allow for optional cryoprotection and freezing in order to obtain diffraction data.

During the incubation in the receiving component, various fields (including, but not limited to, optical, magnetic, and electrical) may be applied to induce nucleation and to control growth of the crystals. The environment of the holding component may also be controlled to optimize the nucleation and growth of crystals. The receiving component may be designed to be substantially impermeable (for example, glass) to components of plugs fluids, carrier fluids, and spacers, and also to the outside elements. Alternatively, the receiving component may be designed to allow permeability of some of the components of plugs fluids, carrier fluids, and spacers, and/or the outside elements. Such permeability may be used to control and optimize nucleation and growth of crystals. For example, selective removal or addition of water through the walls of the holding component (e.g. made of PDMS) may be used to control the rate of nucleation and growth.

These techniques may be incorporated into, for example sparse matrix, gradient, or hybrid screening methods in the context of, for example, microbatch, vapor diffusion and free interface diffusion crystallization methods.

While this disclosure often refers to crystallization of a macromolecule, it should be understood that these methods are equally applicable to crystallization and co-crystallization of several macromolecules, and of their complexes.

The application of the invention described here to crystallization is illustrated using macromolecular crystallization as an example, but it is not limited to the crystallization of macromolecules.

Crystallization of Membrane Proteins

Structural characterization of membrane proteins is an important problem in human health, but structural determination is a challenging problem. The low availability of membrane protein solutions, and the large number of conditions that need to be screened, have contributed to this problem, but are overcome by the present invention. Membrane proteins pose additional challenges due to their hydrophobic transmembrane portion, which typically requires the use of detergents for membrane extraction and crystallization. The presence of detergents can alter the correct formation of aqueous plugs formed in oil-based carrier fluids inside hydrophobic microchannels, unless the surface tensions and wetting are controlled.

Suitable carriers can include those described above. Mixtures of perfluoroamines, such as perfluoro-tri-n-butylamine and perfluoro-tri-n-dibutylmethylamine (also known as FC-40 and FC-70 compounds) can be used as carrier fluids. Such mixtures have been discovered to be useful for formation of plugs when plugs are formed using detergent solutions. This allows plugs containing membrane proteins solubilized in detergent solutions to be conveniently handled using the present invention. Alternatively, other carrier fluids with suitable wetting and surface tension properties may be used. Mixtures of suitable carrier fluids may be prepared in order to tailor properties such as viscosity.

Approaches to Screening for Crystallization Conditions

Sparse matrix screening is often the first step used to find optimal crystallization conditions. A sparse matrix screen is designed to sparsely sample the very large matrix of possible components and concentrations of components that might comprise a solution that facilitates crystallization. The sparse matrix screening method may be implemented by producing an array of plugs in a carrier fluid, optionally separated by spacers. Such plugs may contain a variety of crystallization conditions, including variations in the type and concentration of precipitant, variation of pH and ionic strength, as well as variation of the type and concentration of additives or cryosolvents. Such an array of plugs may be produced as described elsewhere in this application. Preferably, such an array is produced in a holding component by a loading component. A disadvantage of the sparse matrix approach is that only a few concentrations are tested for each reagent or a combination of reagents, and the best crystallization conditions may be missed. A sparse matrix screen samples a large region of chemical space, but it samples it with low density.

The gradient screen is an additional approach that overcomes this disadvantage. A gradient screen is designed to test a range of crystallization conditions such as the concentration of a solution component or the pH of the solution. These gradients are usually designed to test a range of conditions that are known in the art to have a high probability of success, or to test a range of conditions surrounding conditions that have shown indications of success using other screening approaches. Gradient screening can be conveniently implemented by the present invention, as describe elsewhere in this application. A disadvantage of the gradient screening approach is that while it thoroughly explores one range of possible conditions, a large variety of unrelated conditions go untested. A gradient screen samples a smaller region of chemical space, but it samples it with higher density.

A hybrid screening approach may combine the sparse matrix and gradient screen approaches. This approach allows for both the broad screening of possible crystallization conditions with a more complete sampling of conditions likely to prove successful. A hybrid screen may be performed using a holding component that contains plugs with multiple crystallization mixtures, where each mixture is present at several concentrations in several plugs. Generating a large array of plugs, as described in the present invention, allows this hybrid screening approach to be used effectively, facilitating the rapid identification of the ideal or near-ideal crystallization conditions with minimal sample consumption.

All screening approaches may be implemented redundantly, where several substantially identical plugs are used for each crystallization condition. Typically, once an initial holding component is assembled, combined with a protein solution and allowed to incubate in a receiving component, the plugs are observed for signs of crystallization. If, in a first experiment using the present invention, or in a separate experiment using other techniques known in the art, initial conditions amenable to crystallization are determined (for example, by the observation of the formation of crystals too small for structure determination or by observation of ordered precipitate, spherulites, etc.), a subsequent holding component may be designed to optimize the crystal growth conditions. The solutions included in the subsequent holding component for optimization can include a range of conditions surrounding conditions that have shown indications of success, as well as a variety of solutions possessing similar properties as those seen to be successful in the first array of plugs. For example, if a crystalline needle is seen to grow in a plug containing 10% PEG 5000 during an initial screen, a subsequent holding component designed to optimize crystal growth may be designed to produce a concentration gradient of PEG 5000 from about 1% to about 20%, as well as a gradient of other PEGs, such as PEG 2000, PEG 8000, or PEG-MME 5000. Optionally, a series of other crystallization additives not included in the first array of plugs can be included in the subsequent array of plugs. The subsequent array of plugs can be predesigned to be used with proteins having certain defined results in experiment using the first array of plugs, or can be custom designed based upon the results of a specific macromolecule in experiments using the first array.

In order to facilitate such experiments, kits could be assembled that contain holding components with sparse matrix screen reagents along with holding components that contain fine screens for selected conditions present in the sparse matrix screen holding component. In certain alternative embodiments, a holding component could contain a large number of fine screens. This approach, however, would consume more protein than sequentially using a sparse screen holding component followed by one or more selected fine screen holding components.

Computer software may be provided as parts of kits. This software may help analyze the result of the first set of experiments, and then help the user design the next set of experiments. Optionally, this software may contain a database of recipes, and may contain rules for using the results of one set of experiments to design the next set of experiments. Such software may also be used to process the available information of the macromolecule to be crystallized (such as the protein sequence and the method of synthesis and purification), and propose an initial set of crystallization conditions. The software may use this information also during the design of the next set of experiments.

Microbatch Crystallization

To perform microbatch screening, a combining component is used to merge a solution of a macromolecule with an array of plugs in a holding component containing crystallization reagents. The plugs are then transported into a receiving component for incubation and crystal growth. The solution of a macromolecule used can be an array of plugs, or a continuous stream of macromolecule solution. Plugs of solution of a macromolecule can be generated as described elsewhere in this application.

Vapor Diffusion Crystallization

The present invention can be used to perform Vapor Diffusion (VD) Crystallization. In this approach to VD crystallography, it is helpful to think of pairs of plugs in an alternating series, where the plugs are in a carrier fluid optionally containing spacers between members of such a pair and/or between groupings of plugs. In one embodiment, a first set of plugs contain a macromolecule and precipitant solution, and alternate with a second set of "empty" plugs (that is, substantially free of macromolecule) containing a desiccant solution. For example, the desiccant solution may contain the precipitant from the macromolecule and precipitant solution at a higher concentration than in the macromolecule and precipitant solution. During incubation, when the carrier fluid is substantially water-permeable or the plugs are separated by a permeable spacer such as a gas bubble, water molecules will diffuse over time from the first set of plugs with low osmotic pressure to the second "empty" set of dessicant plugs with high osmotic pressure. For example, water will diffuse from a first plug containing a low concentration of macromolecule and precipitant to a second plug containing a high concentration of salt solution, thus increasing the concentration of macromolecule and precipitant in the first plug. This increase in concentration can cause the crystallization of the macromolecule. Crystallization by this technique is not limited, however, to the scenario in which the concentration of the plug containing macromolecule and precipitant increases in concentration. Crystallization can also occur by a decrease in concentration in the plug containing macromolecule, as, for example, when a macromolecule crystallizes due to lowered ionic strength of its solution. This change could be accomplished in an alternative embodiment in which the second "empty" set of plugs has a lower ionic strength than the first set of plugs containing the macromolecule, so water molecules diffuse into the first set of plugs, lowering the ionic strength.

By varying the concentrations of the plug fluids, varied solutions of macromolecule and precipitant can be paired with "empty" plugs containing solutions at a variety of osmotic pressures, allowing the establishment of multiple crystallization experiments within a single device. The rate and the extent of the transfer of water can be controlled by varying the difference in osmotic pressure and the spacing between the plugs in each pair, and by the relative size of the "empty" plugs and the plugs containing macromolecule. Note that the plug fluid in macromolecular crystallization commonly contains water, but it is not limited to water. The solution in the "empty" plugs preferably has an osmotic pressure different from that of the macromolecule and precipitant solution. The "empty" plugs may also contain a different concentration of a component that may be transferred between the "empty" plugs and the crystallization plug.

To create an alternating set of "empty" plugs, in the combining component a stream of macromolecule solution will selectively merge with precipitant plugs but preferably not with the second set of plugs. As described above, the selective merging of precipitant plugs with a stream of macromolecules is possible through the manipulation of relative surface tensions and/or viscosities inside the "empty" plugs and the precipitant plugs, and based on the geometry of the combining component. This system may provide reliable merging with no cross-contamination, as described elsewhere in this application. Preparation of pairs of precipitant plugs and desiccants plugs can be generated by a loading component, controlling the spacing of the plugs as well as the presence or absence of spacers, and loaded into in a holding component as described elsewhere in this application. A solution of macromolecule can then be selectively merged with the precipitant component using a combining component and then incubated in a receiving component.

Note that while this description of vapor diffusion crystallography includes one set of plugs with macromolecule and a second "empty" set of plugs, the method would be operational even if the second set of plugs were not "empty" but instead also contained macromolecule. However the selective merging techniques described here allow the use of smaller quantities of protein.

Free Interface Diffusion Crystallization

Free interface diffusion has the potential to generate well-ordered crystals. The present invention can also be used to perform Free Interface Diffusion (FID) crystallization. To crystallize macromolecules by FID methods, a reservoir of macromolecule solution must be brought into contact with a reservoir of precipitant solution so that a free-standing interface is formed. The reagents mix preferably by simple diffusion and preferably convection is minimized. The convection may be minimized by minimizing the Grashoff number, the ratio of convective to buoyant forces, at the interface. In addition, convection may be minimized by reducing surface tension gradients at the liquid-liquid and liquid-solid interfaces, and increasing viscosity to suppress convective flows.

The present invention comprises a microfluidic method to form a free-interface between two plugs. The two plugs are brought together in a microchannel device, preferably in a receiving component, such that they are partially separated by an immiscible carrier and/or spacer. The plugs are allowed to come into contact at a point where there is no immiscible fluid present, thereby establishing a free-standing interface for fluids and reagents to diffuse between the plugs. In some embodiments, the contact between plugs occurs in a hydrophilic microchannel where the plug fluids wet the wall, bringing the contents of the two plugs into contact and allowing the reagents to mix through a thin fluid interface. A spacer or a volume of the carrier fluid may be used to constrain this interface. In other embodiments, plug fluids may wet a thin filament, establishing an interface.

Methods for controlling the spacing of plugs and the control of wetting of the microchannel by the plug fluids are discussed below.

Plug Manipulation in VD and FID Crystallography

In both FID and VD, the spacing between plugs and the wetting phenomena can be controlled simultaneously by depositing plugs in a separate channel from the channel they are formed in. In one embodiment, first, any sequence of plugs with arbitrary spacing is formed in the first microfluidic device where the plugs do not wet the channel walls. The outlet of the first device is placed into a second device with an inner diameter large enough to contain the first device. The first and second microfluidic devices are translated relative to one another (for example, the first is withdrawn from the second) while plugs are transported out the outlet of the first, and the plugs are subsequently deposited into the second microfluidic device. The surfaces of the second microfluidic device are treated such that the plug fluids are allowed to wet the second device, and to form an interface. The rate at which plugs are deposited and the rate at which the two devices are moved relative to one another determines the spacing between plugs and allow the user to arbitrarily control this spacing.

Additionally, the second microfluidic device may be modified so that wetting is more precisely controlled. Hydrophilic and hydrophobic patches (or other patches that allow variability of the surface energy and can control wetting properties of plug fluids and carrier fluids) may be patterned directly on the inside channel walls so that plugs only wet in limited regions. These patches may be masked, and may be activated upon an external or internal trigger, for example a temperature change or irradiation with light or presence of a particular component in the plug fluid or carrier fluid. Also, a filament, wire, or other surface may be inserted into the microfluidic device with similar patterning to direct wetting only along the length of the filament or wire instead of the walls. The second microfluidic device, if constructed out of glass or another fluid-impermeable material, prevents evaporation of the carrier and reagent fluids.

If the surface of the microchannel is prepared so that wetting is not allowed, the plugs will maintain discrete distances (see FIG. 5a). If wetting by plug fluids is allowed, the plug fluids will come in contact (see FIG. 5b). The surface of the microchannel can have different wetting characteristics. For example, a portion of the microchannel can be hydrophobic. When aqueous plugs are used, this hydrophobic surface would prevent wetting. If another portion of the microchannel is hydrophilic (either on its surface or due to the presence of a hydrophobic fiber), the plug fluids of the alternating plugs will interdiffuse because the hydrophilic surface promotes wetting. Alternatively, wetting of the inner surface of the microfluidics device can be controlled by applying a photoswitchable monolayer. Initially the monolayer would prevent wetting (FIG. 5e), but when activated with light would promote wetting (FIG. 5f).

Several additional examples of methods for bringing two plugs together to form a free-standing interface are shown in FIG. 5. Plugs of reagent solutions are initially formed in a channel under conditions that prevent them from wetting the walls of the channel (FIG. 5a). The conditions are then changed so that the plugs wet the walls (FIG. 5b). If the plugs are sufficiently close, then the wetting phenomena allows the plug fluids to come into contact with each other. For example, aqueous plugs may be transported into a hydrophilic channel but a thin layer of carrier fluid prevents the plugs from wetting while flow is maintained (FIG. 5c). When the flow stops, the thin layer of carrier fluid disperses, allowing the plug fluids to wet the wall (FIG. 5d). As another example, the microchannel walls may be treated with a photoswitchable monolayer that expresses hydrophobic properties initially (FIG. 5e) but then expresses hydrophilic properties upon exposure to a particular wavelength of light (FIG. 5f).

In a further example, the microfluidic system can be formed, in whole or part, from materials that are thermoresponsive. Composite materials with poly(N-isopropylacrylamide) coated on rough silicon substrate are hydrophilic (contact angle of water of ~0°) at low temperatures and hydrophobic (contact angle of water of ~150°) at high temperatures. The hydrophilicity/hydrophobicity transition temperature is between 29° C.~40° C., and the process proceeds within several minutes. Macromolecules may denature at these temperatures, but it is possible to heat the hydrophobic microchannel with the thermoresponsive fiber to above 40° C., quickly cool it to 25° C. (or 18° C. or 4° C.) and inject the macromolecule and precipitant plugs into the microchannel before the transition occurs. After several minutes, the fiber will become hydrophilic and a liquid bridge will form between the macromolecule and precipitant plugs allowing diffusion to occur.

X-Ray Crystallography

The quality of the crystals grown in plugs in a receiving component can be evaluated directly by diffraction at room temperature or other desired temperature (for example, the temperature at which the crystals were grown) in their original mother liquor (FIG. 8). In some embodiments, structural information may be obtained, either from one crystal, or from several crystals either in the same plug or in different plugs. Alternatively, crystals that form in the plugs inside the capillary can be easily extracted, cryoprotected, frozen, and diffracted. Since crystals may be grown at a liquid/liquid interface they would not need to be scraped off a solid surface, minimizing damage.

Figure 3:
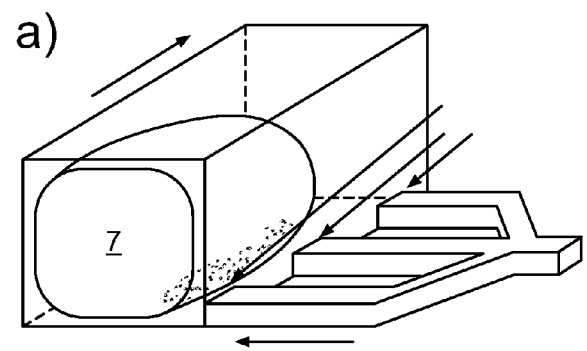
FIG. 3. A schematic illustration of the merging of the array of plugs 7 with another array of protein plugs 13. While an application of this idea to protein crystallization is described below, the same principles may be applied to reactions, assays, and analyses. For example, a set of diverse reactants may arranged in an array of plugs, and then merged with a stream containing the sample.
Figure 3:
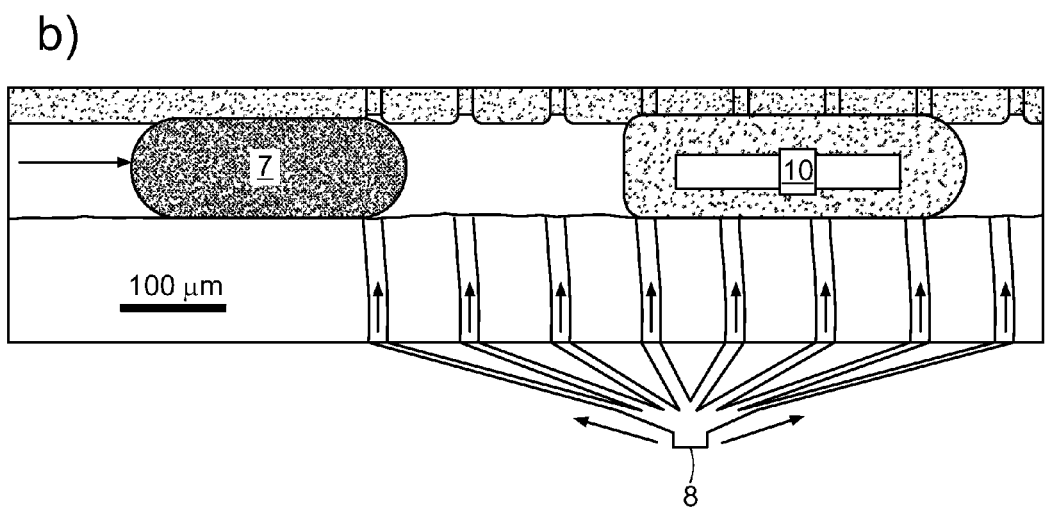
Figure 3:
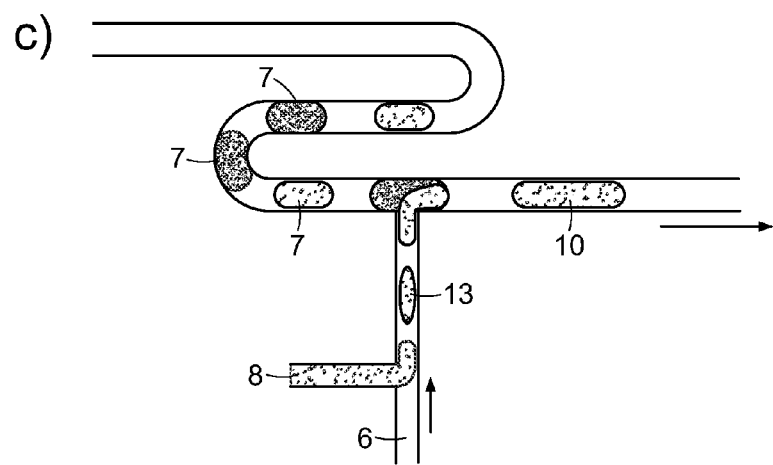

FIG. 3 illustrates a microfluidics device 1 in which various precipitant plugs 7 separated by a carrier 6 are merged with macromolecule plugs 13 separated by a carrier. The precipitant plugs typically have varying concentrations of precipitating agent. The merged plugs 10 then flow through a downstream channel where they can be further manipulated, monitored, collected, etc. The carrier 6 used to separate the precipitant plugs and the macromolecule plugs can be the same or different. FIG. 4c illustrates an example of merging of the protein stream with a series of plugs.

Method of Providing an Array of Plugs

The present invention also provides a method of providing an array of plugs in a holding component to a customer, comprising the steps of offering an inventory of reagents, carrier and plug fluids; receiving from the customer a desired subset of reagents, a desired carrier and a desired plug fluid; forming an array of plugs in a holding component, where plugs are separated from each other with a carrier and where each plug contains an element of the desired reagent subset, and delivering the holding component to the customer. The method can additionally comprise calculating a price for the subset of desired reagents.

The method may involve pre-fabricated arrays of plugs of desired composition, storing these arrays, and providing them to the customer.

The customer may also be provided with a kit comprising a loading component, and a series of holding components, combining components, and receiving components. The components can have integral matching fluidic connections, or separate connectors can be used to link them, or both. The customer may utilize these kits to generate arrays of plugs of desired composition. Reagents both proprietary to the customer and non-proprietary may be used.

The inventory of reagents, carriers and plug fluids can be offered as a catalog either in paper or electronic form (in some embodiments accessible via the internet). Suitable reagents, carriers and plugs fluids are described throughout the present disclosure. For protein crystallography, the reagents can include any compound used to screen for crystal formation. For example, reagents can include precipitation agents, additives, cryosolvents, buffering agents, etc.

For example, a list of companies and products relating to reagents and kits for protein crystallography is described at http://www.structmed.cimr.cam.ac.uk/Course/Crystals/screening.html.

In this method, the customer selects various features of the array of plugs within the holding device: such as one or more precipitation agents, the carrier, the plug fluid, the pH of the plug fluid, additives, cryosolvents, etc.

For membrane proteins and other macromolecules, the plug fluid can be a lipidic cubic phase (see e.g. Landau, E. M. & Rosenbusch, J. P. Lipidic cubic phases: A novel concept for the crystallization of membrane proteins. Proceedings of the National Academy of Sciences of the United States of America 93, 14532-14535 (1996), and Nollert, Methods. 34(3):348-53 (November 2004)).

A nonexclusive list of salts that may be used as precipitation agents is as follows: tartrates (Li, Na, K, Na/K, $NH_4$); phosphates (Li, Na, K, Na/K, $NH_4$); acetates (Li, Na, K, Na/K, Mg, Ca, Zn, $NH_4$); formates (Li, Na, K, Na/K, Mg, $NH_4$); citrates (Li, Na, K, Na/K, $NH_4$); chlorides (Li, Na, K, Na/K, Mg, Ca, Zn, Mn, Cs, Rb, $NH_4$); sulfates (Li, Na, K, Na/K, $NH_4$); maleates (Li, Na, K, Na/K, $NH_4$); glutamates (Li, Na, K, Na/K, $NH_4$); tetraarylborates (Li, Na, K, Na/K, $NH_4$).

A nonexclusive list of organic materials that may be used as precipitation agents is as follows: PEG 400; PEG 1000; PEG 1500; PEG 2K; PEG 3350; PEG 4K; PEG 6K; PEG 8K; PEG 10K; PEG 20K; PEG-MME 550; PEG-MME 750; PEG-MME 2K; PEGMME 5K; PEG-DME 2K; dioxane; methanol; ethanol; 2-butanol; n-butanol; t-butanol; jeffamine m-600; isopropanol; 2-methyl-2,4-pentanediol; 1,6-hexanediol.

Solution pH can be varied by the inclusion of buffering agents; typical pH ranges for biological materials lie anywhere between values of 3 and 10.5 and the concentration of buffer generally lies between 0.01 and 0.25 M. The microfluidic devices described in this document are readily compatible with a broad range of pH values, particularly those suited to biological targets.

A nonexclusive list of possible buffers that may be used according to the invention is as follows: Na-acetate; HEPES; Na-cacodylate; Na-citrate; Na-succinate; Na—K-phosphate; TRIS; TRIS-maleate; imidazole-maleate; bistrispropane; CAPSO, CHAPS, MES, and imidazole.

Additives are small molecules that affect the solubility and/or activity behavior of the target. Such compounds can speed up crystallization screening or produce alternate crystal forms or polymorphs of the target. Additives can take nearly any conceivable form of chemical, but are typically mono and polyvalent salts (inorganic or organic), enzyme ligands (substrates, products, allosteric effectors), chemical crosslinking agents, detergents and/or lipids, heavy metals, organometallic compounds, trace amounts of precipitating agents, and small molecular weight organics.

The following is a nonexclusive list of additives that may be used in accordance with the invention: 2-butanol; DMSO; hexanediol; ethanol; methanol; isopropanol; sodium fluoride; potassium fluoride; ammonium fluoride; lithium chloride anhydrous; magnesium chloride hexahydrate; sodium chloride; calcium chloride dihydrate; potassium chloride; ammonium chloride; sodium iodide; potassium iodide; ammonium iodide; sodium thiocyanate; potassium thiocyanate; lithium nitrate; magnesium nitrate hexahydrate; sodium nitrate; potassium nitrate; ammonium nitrate; magnesium formate; sodium formate; potassium formate; ammonium formate; lithium acetate dihydrate; magnesium acetate tetrahydrate; zinc acetate dihydrate; sodium acetate trihydrate; calcium acetate hydrate; potassium acetate; ammonium acetate; lithium sulfate monohydrate; magnesium sulfate heptahydrate; sodium sulfate decahydrate; potassium sulfate; ammonium sulfate; di-sodium tartrate dihydrate; potassium sodium tartrate tetrahydrate; di-ammonium tartrate; sodium dihydrogen phosphate monohydrate; di-sodium hydrogen phosphate dihydrate; potassium dihydrogen phosphate; di-potassium hydrogen phosphate; ammonium dihydrogen phosphate; di-ammonium hydrogen phosphate; tri-lithium citrate tetrahydrate; tri-sodium citrate dihydrate; tri-potassium citrate monohydrate; diammonium hydrogen citrate; barium chloride; cadmium chloride dihydrate; cobaltous chloride dihydrate; cupric chloride dihydrate; strontium chloride hexahydrate; yttrium chloride hexahydrate; ethylene glycol; Glycerol anhydrous; 1,6 hexanediol; MPD; polyethylene glycol 400; trimethylamine HCl; guanidine HCl; urea; 1,2,3-heptanetriol; benzamidine HCl; dioxane; ethanol; iso-propanol; methanol; sodium iodide; L-cysteine; EDTA sodium salt; NAD; ATP disodium salt; D(+)-glucose monohydrate; D(+)-sucrose; xylitol; spermidine; spermine tetra-HCl; 6-aminocaproic acid; 1,5-diaminopentane diHCl; 1,6-diaminohexane; 1,8-diaminooctane; glycine; glycyl-glycyl-glycine; hexaminecobalt trichloride; taurine; betaine monohydrate; polyvinylpyrrolidone K15; non-detergent sulfo-betaine 195; non-detergent sulfo-betaine 201; phenol; DMSO; dextran sulfate sodium salt; Jeffamine M-600; 2,5 Hexanediol; (+/−)-1,3 butanediol; polypropylene glycol P400; 1,4 butanediol; tert-butanol; 1,3 propanediol; acetonitrile; gamma butyrolactone; propanol; ethyl acetate; acetone; dichloromethane; n-butanol; 2,2,2 trifluoroethanol; DTT; TCEP; nonaethylene glycol monododecyl ether, nonaethylene glycol monolauryl ether; polyoxyethylene (9) ether; octaethylene glycol monododecyl ether; octaethylene glycol monolauryl ether; polyoxyethylene (8) lauryl ether; Dodecyl-β-D-maltopyranoside; Lauric acid sucrose ester; Cyclohexyl-pentyl-β-D-maltoside; Nonaethylene glycol octylphenol ether; Cetyltrimethylammonium bromide; N,N-bis(3-D-gluconamidopropyl)-deoxycholamine; Decyl-γ-D-maltopyranoside; Lauryldimethylamine oxide; Cyclohexyl-pentyl-β-D-maltoside; n-Dodecylsulfobetaine, 3-(Dodecyldimethylanimonio)propane-1-sulfonate; Nonyl-β-D-glucopyranoside; Octyl-β-D-thioglucopyranoside, OSG; N,N-Dimethyldecylamine-μ-oxide; Methyl 0-(N-heptylcarbamoyl)-α-D-glucopyranoside; Sucrose monocaproylate; n-Octanoyl-β-D-fructofuranosyl-α-D-glucopyranoside; Heptyl-β-D-thioglucopyranoside; Octyl-β-D-glucopyranoside, OG; Cyclohexyl-propyl-β-D-maltoside; Cyclohexylbutanoyl-N-hydroxyethylglucamide; n-decylsulfobetaine, 3-(Decyldimethylammonio)propane-1sulfonate; Octanoyl-N-methylglucamide, OMEGA; Hexyl-β-D-glucopyranoside; Brij 35; Brij 58; Triton X-114; Triton X-305; Triton X-405; Tween 20; Tween 80; polyoxyethylene(6)decyl ether; polyoxyethylene (9)decyl ether; polyoxyethylene(10)dodecyl ether; polyoxyethylene(8)tridecyl ether; Decanoyl-N-hydroxyethylglucamide; Pentaethylene glycol monooctyl ether; 3-[(3-cholamidopropyl)-dimethylammonio]-1-propane sulfonate; 3-[(3-Cholamidopropyl)-dimethyl ammonio]hydroxy-1-propane sulfonate; Cyclohexylpentanoyl-N-hydroxyethylglucamide; Nonanoyl-N-hydroxyethyglucamide; Cyclohexylpropanol-N-hydroxyethylglucamide; Octanoyl-N-hydroxyethylglucamide; Cyclohexylethanoyl-N-hydroxyethylglucamide; Benzyldimethyldodecyl ammonium bromide; n-Hexadecyl-β-D-maltopyranoside; n-Tetradecyl-β-D-maltopyranoside; n-Tridecyl-β-D-maltopyranoside; Dodecylpoly(ethyleneglycoether); n-Tetradecyl-N,N-dimethyl ammonio-1-propanesulfonate; n-Undecyl-β-D-maltopyranoside; n-Decyl D-thiomaltopyranoside; n-dodecylphosphocholine; α-D-glucopyranoside, β-D-fructofuranosyl monodecanoate, sucrose mono-caprate; 1-s-Nonyl-β-D-thioglucopyranoside; n-Nonyl-β-D-thiomaltoyranoside; N-Dodecyl-N,N-(dimethlammonio)butyrate; n-Nonyl-β-D-maltopyranoside; Cyclohexyl-butyl D-maltoside; n-Octyl-β-D-thiomaltopyranoside; n-Decylphosphocholine; n-Nonylphosphocholine; Nonanoyl-N-methylglucamide; 1-s-Heptyl-β-D-thioglucopyranoside; n-Octylphosphocholine; Cyclohexyl-ethyl D-maltoside; n-Octyl-N,N-dimethyl ammonio-1-propanesulfonate; Cyclohexyl-methyl-β-D-maltoside.

Cryosolvents are agents that stabilize a target crystal to flash-cooling in a cryogen such as liquid nitrogen, liquid propane, liquid ethane, or gaseous nitrogen or helium (all at approximately 100-120° K) such that a crystal becomes embedded in a vitreous glass rather than ice. Any number of salts or small molecular weight organic compounds can be used as a cryoprotectant, and typical ones include but are not limited to: MPD, PEG-400 (as well as both PEG derivatives and higher molecular-weight PEG compounds), glycerol, sugars (xylitol, sorbitol, erythritol, sucrose, glucose, etc.), ethylene glycol, alcohols (both short- and long chain, both volatile and nonvolatile), LiOAc, LiCl, $LiCHO_2$, $LiNO_3$, $Li_2SO_4$, $Mg(OAc)_2$, NaCl, $NaCHO_2$, $NaNO_3$, etc. Again, materials from which microfluidics devices in accordance with the present invention are fabricated may be compatible with a range of such compounds.

In addition to chemical variability, a host of other parameters can be varied during crystallization screening. Such parameters include but are not limited to: (1) volume of crystallization trial; (2) ratio of target solution to crystallization solution; (3) target concentration; (4) cocrystallization of the target with a secondary small or macromolecule; (5) hydration; (6) contact surfaces; (7) modifications to target molecules; etc.

For application (4), cocrystallization, the array may represent a subset of small molecules that span a portion of chemical space. Alternatively, the array may represent a subset of oligonucleotides spanning a genome or a portion of a genome.

Other Applications

The present invention may be used for any experiments in which a large variety of reactions are to be performed in parallel, for example, any applications which are currently typically applied in 96-, 384- or 1536-well plates. Holding components as described in the present invention may be prepared for any of these applications.

One such application is combinatorial chemistry. A holding component may be prepared that contain a diversity of reagents to be reacted with a second reagent or set of reagents after combination in a combining component. These reagents are not limited to being in solution, and may be also presented on beads or in other forms. Typical applications of combinatorial chemistry include the synthesis of a diversity of compounds to be tested for pharmaceutical or agricultural activity. Another application is the synthesis of a diversity of inorganic, organic, or organometallic catalysts. For example, the holding component may contain a number of different potential ligands for a metal, and after combination with a metal or variety of metals in the combining component, the ligands are allowed to react with the metal or metals to provide an array of plugs containing the potential catalysts. Subsequently the plugs may be combined with a test reagent in a second combining component to allow the catalysts to be tested for catalytic activity. Combinatorial chemistry reagents in a holding component will be chosen such that, after being combined with a second reagent or sent of reagents and allowed to react, the final products will span a desired region of chemical space. In addition, the plugs in the holding component may contain reagents in a suspension. This may be useful for increased stability, or when solubility is limited. The holding component may also be frozen for increased stability.

Another application is the screening of a diverse library of compounds for a desired property, frequently referred to as "high-throughput screening". For example, if a catalyst is needed to carry out a specific reaction to convert substance A to substance B, a number of potential catalysts can be loaded into a holding component, combined with substance A, allowed to react, and then the resulting plugs in a receiving component can be monitored for the presence of substance B. In this example, the catalyst could be inorganic, organometallic, organic, enzymatic or comprised of nucleic acids. Alternatively, a holding component could contain a diverse set of reactants in order to test the activity of a potential catalyst. In a combining component, the reactant set would be combined with a potential catalyst and allowed to react in a receiving component. The course of the reactions would then be monitored, for example by UV-vis spectroscopy, fluorescence, or mass-spectroscopy, to determine the reactivity of the catalyst.

Similarly, diverse sets of compounds or "libraries" can be loaded in a holding component to be tested for a desired biological activity, such as for use as a pharmaceutical or agricultural compound. Examples of typical libraries include a set of over 10,000 plant and microbial extracts offered by Sigma-Aldrich and PhytoMyco Research Corporation, the Library of Pharmacologically-Active Compound (Product No. LO1280) offered by Sigma-Aldrich, and compounds from the Aldrich Library of Rare Chemicals. Other examples include the Pharma Library Collection offered by Nanosyn, Inc., that includes compounds preselected for their potential to be drugs based on their known properties and the Explore Library Collection, also from Nanosyn, Inc., that contains more reactive compounds. Other examples include Double Diversity arrays by Nikem Research, which contain a single reactive functional group to allow attachment of a customer's proprietary compounds, and Nikem's coMerge arrays.

Other uses and examples of compound libraries are described in U.S. Pat. No. 6,740,506, incorporated herein by reference. In addition, a holding component can comprise libraries synthesized via directed evolution such as those described in U.S. Pat. No. 6,740,506.

Similarly, the holding component can contain a diversity of biomolecules. For example, as described below in Example 10 a holding component could comprise a diverse set of proteins for testing for binding to, or reacting with, a single substrate or a set of substrates. An example of a protein library is described in Tsuji et al., Nucleic Acids Research 29(20):e97 (2001). The holding component could also contain a library of proteins expressed by a genome. Similarly, a holding component could contain oligopeptides or oligo- or poly-saccharides. Alternatively, a holding component could contain nucleic acids, such as DNA or RNA.

In one set of embodiments, a holding component could contain a set of biomolecules derived from a complete genome of any organism, including animals, fungi, Archaea, bacteria, plants, mammals, humans, etc., that has been sequenced by means known in the art. A holding component could contain biomolecules representing the entire genome of an organism, or a subset of the genome. For example, the holding component could contain nucleic acids representing a genome of an organism. The nucleic acids could be RNA, DNA, cDNA or EST clones. One example is the ez-Rays™ human Oligonucleotide Library sold by Matrix Technologies which contains over 15,000 50-mer DNA probes targeted to human mRNA sequences plus control probes.

In another set of embodiments, the holding component could contain live cells. For example, useful sets of cells include a deletion library containing a large set of deletion mutants of an organism, such as that produced by the Saccharomyces Genome Deletion Project (Giaever et al., Nature. 418(6896):387-91 (2002)). Other useful cell collections include sets of EST clones, BAC clones, ORF clones and PAC clones, for example as offered by Invitrogen Corporation. In other embodiments, a single type of cell could be offered in a holding component for combining with a plurality of reagents. For example, hepatic cells, such as those described in O'Connor, et al., Cytometry A. 63(1):48-58 (2005), could be loaded in a holding component, and then combined in a combining component with a diversity of potential pharmaceuticals. Subsequent monitoring of cell activity or viability could be used to test for liver toxicity. Alternatively, a variety of cell lines representing subpopulations, also described in O'Connor, et al., Cytometry A. 63(1):48-58 (2005), could be loaded into a holding component.

For either high-throughput screening or combinatorial chemistry applications, an entire library of thousands of compounds could be offered in a single holding component. Alternatively, as described above for protein crystallography, a sparse subset of the entire library could be offered in a single holding component, and then finer subsets of the entire library could be offered for use after a particular region of a chemical space has been found to have desirable properties.

In another set of embodiments, the holding component could be used for diagnostics and detection. Non-limiting example include medical diagnostics, veterinary diagnostics, the testing of crops, animals, and farm products, and environmental testing including the testing of water and air. Preferably, the holding component contains a plurality of tests, and/or multiple copies of the same test. The holding component can also contain control experiments.

In some embodiments of the invention, after an initial test using a specific holding component containing a sparse library of substances, a second custom holding component could be prepared containing substances close in properties (that is close in chemical space) to "hits" found in the initial test. This process could be iterated indefinitely.

EXAMPLES

In the examples below, glass capillaries were silanized to render them hydrophobic.

Example 1: No-Loss Injection of Sub-µL Volumes of Solutions into Microfluidic Devices A 10 µL syringe and a piece of Teflon tubing were filled with the perfluoroamine, followed by aspiration of a small volume (less than 1 µl) of a membrane protein solution. Because the perfluoroamine carrier fluid preferentially wet the Teflon, it formed a thin layer between the protein and Teflon, preventing sticking of the protein solution to the walls of the tubing and allowed for complete, no-loss dispensing into a microfluidic device.

Example 2: Forming an Array of Plugs of Different Composition in a Holding Component In this experiment, array of plugs containing different composition were generated in Teflon tubing or in glass capillaries. A piece of Teflon tubing (OD: 760 µm, ID: 305 µm) was attached to the needle of a 5 µL syringe (Hamilton). Another piece of Teflon tubing with smaller diameter (OD: 250 µm, ID: 200 µm) was attached to the large Teflon tubing and sealed by either epoxy or wax. Oil (FC-3283/PFO at 50:1) was aspirated into the tubing and the syringe. The tubing was immersed into an aqueous solution of composition A (solution A), and the plunger was pulled back to aspirate a small amount (0.1-0.5 µl) of solution A. Next the tubing was immersed into the oil and the same amount of oil was aspirated into the tubing. This two-step aspiration process was repeated for solution B, C, . . . until all the solutions were used, and an array of plugs of composition of A, B, . . . was formed inside the Teflon tubing.

To form such an array of plugs in a glass capillary, the Teflon tubing was inserted into the wide end of a Hampton Research glass capillary (OD 200 µm, ID 180 µm, with an approximately 2 mm-wide opening in a shape of a funnel on one end). After the whole system (the syringe, the Teflon tubing and the capillary) was filled with oil, equal amount of solution A, oil, solution B, oil, . . . were aspirated into the capillary following the same procedure as described above.

When the array of plugs was formed inside the Teflon tubing, the Teflon tubing was cut off and frozen with the liquid inside. The freezing process prevented liquid loss by permeation though Teflon, thus help the long-term storage of the plugs. When the array of plugs was formed inside the glass capillary, the capillary was removed from the Teflon tubing and sealed with wax. In this way plugs could be stored for a long time (over 6 months).

Example 3: Transporting the Array of the Plugs into a PDMS Microchannel

In this experiment, the array of the plugs stored inside the Teflon tubing or the glass capillary (holding component) was transported into a PDMS microchannel (receiving component).

Three different configurations were used. In the first configuration, the inlet of the PDMS microchannel was coupled to a glass capillary obtained from Hampton research. This capillary was used as an adapter and it had a shape of a funnel. The small end of the capillary was inserted into the PDMS microchannel and the gap between the capillary and the wall of the PDMS microchannel was filled with half-cured PDMS. After incubation at 110° C. for 5 min, the half-cured PDMS was solidified and the junction became leak-proof. The capillary that had the array of the plugs inside was firmly inserted into the larger end of the adapter capillary. The connection was leak-proof without any sealing. By tilting the whole setup, the gravity force would pull the array of the plugs into the PDMS microchannel. Alternatively, the transportation of the plugs could be achieved by using a syringe to apply a pressure on the open end of the capillary containing the array.

In the second configuration, the inlet of the PDMS microchannel was coupled to a small Teflon tubing (OD: 250 μm, ID: 200 μm). The junction was made leak-proof in the same way as described in the first configuration (using half-cured PDMS). The free end of the Teflon tubing was then inserted into the larger end of the glass capillary that held the array of the plugs. Again, either the gravity force or a pressure on the small end of the glass capillary applied by a syringe was applied to transfer the array of the plugs into the PDMS microchannel.

In the third configuration, the array of the plugs was first transported into a piece of small Teflon tubing that was connected to a syringe in the same setup as above. Then the small Teflon tubing with the array of the plugs inside was inserted into the capillary coupler. By applying pressure through the syringe, the array of the plugs can be pushed into the PDMS microchannel.

The flow of the plugs may be controlled by the syringe that pushed the plugs into the microchannel. Alternatively, after the array of the plugs entered the PDMS microchannel and passed the oil inlet, the inlet may be sealed by wax. Then the movement of the plugs can controlled by the flow of the oil, which was pushed by a syringe and a syringe pump.

Example 4: Transporting the Plugs from a PDMS Channel (Receiving Component) into a Glass Capillary (Holding Component)

In this experiment, the array of the plugs that has been merged with protein solution individually was transported into a glass capillary that was connected to the outlet of the PDMS microchannel. A reusable configuration could be employed here to reuse the PDMS microfluidic device. This was achieved by attaching a thin-walled (OD: 250 μm, ID: 200 μm) Teflon tubing to the outlet of the PDMS microchannel. The glass capillary (OD: 200 μm, ID: 180 μm) from Hampton research can be coupled to the Teflon tubing by inserting the free end of the tubing to the larger end of the glass capillary. No sealing is needed for the coupling and no leaking was observed. After one glass capillary was filled with one array of the plugs that contain the mixture of the protein solution and the various precipitants, it was pulled off from the Teflon tubing and sealed by wax. Another glass capillary can be used to couple to the Teflon tubing for the next array of the plugs.

Example 5: Merging Each Plug in the Array with a Protein Solution in a PDMS Microchannel In this experiment, there are two configurations to carry out the merging. In the first configuration, the array of plugs was pushed in a merging component, +past a junction with a channel into which was flowed a stream of the protein solution. Each plug would merge with a small amount of protein solution. By varying the flow rate of the plugs or the flow rate of the protein stream, the relative volume ratio of each precipitant to protein can be controlled.

In the second configuration, the protein stream was first injected into a flow of oil so that another array of plugs of protein solution was formed. The array of the plugs containing the precipitants can be brought to merge with the array of the plugs of protein solution one by one at a T-junction in a merging component.

Example 6: Merging Every Other Plug with Protein Solution in a PDMS Microchannel An array of the plugs may be composed of many groups of plugs. It is sometimes desirable for the combining component to merge a solution selectively amongst these groups. For example, in the case of VD crystallography, a first group of plugs would contain a precipitant solution, while a second group of plugs would contain a desiccant solution. To perform crystallization by vapor diffusion, it is desirable for a stream of the protein solution to merge with precipitant plugs but not desiccant plugs. The merging of an array of plugs with a reagent solution can be described by the Capillary number, which is dependent on surface tension and viscosity. In the preferred embodiment, the surface tensions between the plugs and the carrier fluid can be controlled, allowing for control of selective merging. Surface tension can be modified through manipulation of surfactant concentrations inside the plugs. Viscosity may be also controlled, for example by adding components that would renfer the desiccant plugs viscous (for example, polyethylene glycols). In other embodiments, flow rates of the array of the plugs and the protein stream may also be used to control of selective merging.

A series of experiments demonstrating selective merging using precipitant solutions and detergent solutions were performed. In the first experiment, a plug containing precipitants merged with a stream of 1% solution of octyl-β-D-glucopyranoside (OG) detergent. In a second experiment, performed on a separate but identical device to that used in the first experiment, and at the same flow rates, a desiccant plug, containing polyethylene glycol 5000 monomethylether and a mixture of semi-fluorinated and non-fluorinated surfactants, bent around a stream of 1% OG, and did not merge. In a third experiment, in which a stream of 1% OG was used in a combining component along with an array of precipitant plugs alternating with desiccant plugs, the stream of 1% OG merged with only the precipitant plugs.

Therefore, the salt concentration in the plug that is not merged can be higher than that in the plug that is merged. If the oil is water permeable, the osmotic pressure resulting from the concentration different can force water to diffuse from the merged plugs to the unmerged plugs. The merged plugs can be concentrated in this way and protein nucleation and crystallization can be enhanced.

Example 7: Crystallization of a Membrane Protein

Fatty acid amide hydrolase (FAAH) is an integral membrane protein that degrades endocannabinoid signaling molecules at neuron surfaces. FAAH removal is associated with increased analgesic effects; therefore, it is considered a prime drug target for the relief of pain and related neurological disorders. The structure of rat FAAH complexed with an arachidonyl inhibitor is known. The complex showed how FAAH is integrated into cell membranes and how it establishes access to the bilayer from its active site.

FAAH crystals were generated on chip using the microbatch method of protein crystallization. A composite PDMS-teflon capillary device with three aqueous inlets and one carrier fluid inlet was constructed. This device had the capillary inserted from the outlet directly up to the carrier fluid-aqueous junction, to facilitate the formation of plugs containing membrane protein surfactants. The carrier fluid used was perfluorotripentylamine (3M FC-70), which we have shown to be compatible with membrane protein surfactants. Using this device, ~40 cm of tubing was filled with the microbatch droplets. A gradient of precipitant concentrations in the plugs was achieved by varying the flow rates of the precipitant and buffer streams. The precipitant solution for FAAH complexed with the arachidonyl inhibitor was composed of 16% PEG 6000, 200 mM $Li_2SO_4$, 10% ethylene glycol, 14% 2-methyl-2,4-pentanediol and 200 mM citrate buffered at a pH of 5.6. The precipitant for FAAH in its apo form was 24% PEG 4000, 200 mM $Li_2SO_4$, 10% 2-methyl-2,4-pentanediol, 400 mM NaCl and 100 mM Tris buffered at a pH of 8.2.

Example 8: VD Crystallization Screen: Preparation and Transportation of an Array of Plugs First a small piece of Teflon tubing (outer diameter 250 μm, inner diameter 200 μm) was connected to a 10 μL syringe (Hamilton). This connection was made by using a "tube within tube" method. A thicker piece of Teflon tubing (approximately 30G) was connected to the syringe, and the thing piece of tubing was inserted into the thicker piece, and the connection was sealed (for example with was). The pieces of tubing could be stretched to reduce their diameter. The syringe and the Teflon tubing were filled with fluorocarbon carrier fluid. The fluorocarbon is a mixture of perfluoroperhydrophenanthrene (PFP) and 1H,1H,2H,2H-perfluorooctanol (PFO) at volume ratio of 10:1. To prepare an array of plugs, different reagents, fluorocarbon, and air bubbles were aspirated successively into the piece of small Teflon tubing. This is achieved by pulling the plunger of the syringe that was connected with the Teflon tubing while the other end of the Teflon tubing was in the corresponding solution. During the aspiration process, the movement of the plunger was controlled by a manual micrometer syringe driver (Stoelting Co.). Before the aspiration of each reagent, a small amount of fluorocarbon was aspirated into the Teflon tubing to separate the plugs. In most experiments, an air bubble was also aspirated into the Teflon tubing after the fluorocarbon aspiration. These bubbles prevented accidental coalescence of plugs containing solutions of contrasting viscosities. After the array of the plugs was prepared inside the Teflon tubing, more fluorocarbon was aspirated into the tubing. The Teflon tubing was then inserted into a funnel-shaped capillary (Hampton Research). By pushing the plunger of the syringe that was connected to the Teflon tubing, the array of the plugs was transferred into the capillary (OD 0.20 mm, ID 0.18 mm). The capillary was then cut off from the tubing and sealed by wax for long-term storage. To utilize the array for experiments in microfluidic channels, it was first transported from the capillary into the Teflon tubing. The Teflon tubing was then inserted into a funnel-shaped adapter that was coupled to the inlet of the microfluidic channel. The transportation of the array was controlled by the syringe that was connected to the Teflon tubing. At the same time, a stream of the target solution was injected into the side channel and this stream merged with the array of the plugs, mixed, and the reaction occurred. The array of the plugs after mixing was transported into a capillary using a similar funnel-shaped adapter. After the capillary was filled with the array of the plugs, the capillary could be taken off the microfluidic channel and sealed for incubation or analysis.

Example 9: Functional Assay of Several Enzymes Against One Substrate

An array of plugs was prepared, which contained alkaline phosphatase (AP) (0.02 mg/ml in 0.2 M diethanol amine, pH 10.5), catalase (0.02 mg/ml in PBS, pH 7.3), ribonuclease A (RNase) (0.02 mg/ml in 0.05 M Tris buffer, pH 7.5), and lysozyme (0.02 mg/ml in 0.05 M NaAc buffer, pH 4.5). The array had one plug of each enzyme, and every two neighboring enzyme plugs were separated by two plugs of PBS buffer. These plugs served as "washer plugs", removing any cross-contamination of the substrate stream (this cross-contamination could occur during merging with the stream of substrate if an enzyme was transported by diffusion or surface tension-driven flow into the stream of the substrate). An air bubble was inserted between every two neighboring aqueous plugs. To assay the activity of the four enzymes on the substrate fluorescein diphosphate (FDP) (11 μM with 0.5 M NaCl), the array of plugs was merged with the solution of FDP at a T-junction (See FIG. 11). The flow rates of the array and the FDP stream were 1.2 μL/min and 0.5 μL/min, respectively. The array of the merged plugs was collected in a capillary and the fluorescence image of each plug was taken by a fluorescence microscope (Leica DMIRE2) equipped with a digital camera (Hamamatsu, ORCA-ER). Fluorescence intensity in the images was analyzed using Metamorph Imaging System (Universal Imaging), indicating the activity of alkaline phosphatase.

Example 10: VD Crystallization Screen: Screening Precipitants for Crystallization Conditions of Thaumatin To screen the 48 precipitants from the Crystal Screen kit (Hampton Research), an array of 48 plugs of 48 precipitants (from No. 1 to No. 48) was prepared. The reagent formulation of the precipitants can be found at the website of Hampton Research (http://www.hamptonresearch.com/support/guides/2110F.pdf). The precipitant reagents had various salt concentrations (e.g., No. 44 0.2 M ammonium formate and No. 33 4.0 M sodium formate) and various viscosities (e.g., No. 30, 30% w/v PEG 8000). Every two neighboring plugs were separated by an air bubble. The carrier fluid was the mixture of PFP and PFO (volume ratio 10:1). After the array was prepared, it was transported into the microchannel for screening. Another piece of Teflon tubing was connected to a 10 µL syringe and the syringe+tubing assembly was filled with PFP. Slightly less than 1.0 µL solution of thaumatin (60 mg/mL in 0.1 M N-(2-acetamido)iminodiacetic acid buffer, pH 6.5) was aspirated into the tubing. The tubing was then inserted into the inlet of the side microchannel of the T-junction. The solution of thaumatin was driven into the main channel and merged with the array of the plugs of precipitants. The flow rates of the thaumatin solution and the array were 0.5 µL/min and 1.2 µL/min, respectively. After the plugs were merged with thaumatin solution, they were collected in a capillary and sealed by wax for incubation. Incubation of the plugs at 18° C. resulted in crystallization of thaumatin in plugs that contained precipitant No. 29 and thaumatin. Less than ~0.1 µL of thaumatin solution remained in the channel. This method does not require large volumes of solution and does not generate much waste, and is useful with volumes as low as sub-microliter, screened against nanoliter plugs of multiple reagents.

To screen the five precipitants from the Crystal Screen kit, an array of plugs was prepared, which contained five different precipitants from the screening kit: No. 13 (0.2 M sodium citrate/0.1 M tris HCl/30% v/v PEG 400, pH 8.5), No. 24 (0.2 M CaCl2/0.1 M NaAc/20% v/v isopropanol, pH 4.6), No. 25 (0.1 M imidazole/1.0 M NaAc, pH 6.5), No. 29 (0.1 M HEPES/0.8 M potassium sodium tartrate, pH 7.5), and No. 33 (4.0 M sodium formate). The array had two plugs of each precipitant and totally ten plugs. An air bubble was inserted between every two neighboring plugs. The mixture of PFP and PFO (volume ratio 10:1) was used as the carrier fluid. An aqueous stream of thaumatin (~60 mg/ml in 0.1 M ADA buffer, pH 6.5) was injected into the array of the plugs for crystallization. The flow rates of the array and the stream of thaumatin were 1.2 µL/min and 0.5 µL/min, respectively. Incubation of the plugs at 18° C. resulted in crystallization of thaumatin in plugs that contained precipitant No. 29 and thaumatin.

Example 11: Free-Interface Diffusion Crystallization Screen

Free interface diffusion trials were set up by alternating protein plugs with precipitant plugs. The alternating pairs of plugs were pumped into a piece of narrow Teflon tubing, prior to being transferred to a sealed capillary. (The sealed capillary was rendered hydrophobic by silanization). A hydrophilic glass fiber was inserted into the capillary. The capillary was moved at a constant rate to control the distance between the plugs as they were deposited. The droplets spontaneously wetted the glass fiber forming a small interconnection between the drops allowing diffusion to occur.

Example 12: Free-Interface Diffusion Crystallization Screen

A Teflon capillary (ID 0.008±0.001 in.; wall 0.001±0.001 in.) was filled with a 5:1 v/v mixture of 3M FC-3283:1H, 1H,2H,2H-perfluoro-1-octanol. A ~300 nL plug of 25 mg/mL thaumatin in ADA buffer was aspirated into the capillary followed by a small ~200 nL slug of the fluorocarbon mixture, a ~300 nL plug of 2 M sodium/potassium tartrate, and another slug of the fluorocarbon mixture, in that order. The open ends of the capillary were sealed with capillary wax, and the capillary was secured in an eppendorf 5415 D centrifuge such that the accelerating force was exerted approximately normal to the length of the capillary. (The capillary was placed on the rotor and secured with tape to the top of centrifuge tubes.) Centrifugation was applied at 2000 rpm for 30 s. The centrifugation process dispelled the denser carrier fluid from between the two aqueous plugs, allowing the two aqueous plugs to come together and establish an interface. Solutes mixed diffusively across the interface, and a precipitate was observed at the interface between the two aqueous plugs immediately after centrifugation. One day later, crystals of the protein thaumatin formed.

The invention claimed is:

1. A method for manipulating droplets of a sample fluid, the method comprising:
   flowing droplets of the sample fluid in a same direction in an immiscible carrier fluid within a main microfluidic channel comprising a region comprising one or more side branch channels, wherein each droplet is separated from an immediately adjacent droplet by immiscible carrier fluid; and
   increasing spacing between a pair of immediately adjacent droplets flowing through the region by adding a volume of immiscible carrier fluid between only the pair of immediately adjacent droplets via one of the side branch channels, wherein the pair of immediately adjacent droplets remain intact while flowing through the region and continue to flow within the main microfluidic channel downstream of the region; or
   reducing spacing between a pair of immediately adjacent droplets flowing through the region by removing a volume of immiscible carrier fluid from only between the pair of immediately adjacent droplets via an active flow controllable component operably coupled to one of the side branch channels that causes a volume of immiscible carrier fluid between only the pair of immediately adjacent droplets to flow into the side branch channel, wherein the pair of immediately adjacent droplets remain intact while flowing through the region and continue to flow within the main microfluidic channel downstream of the region.

2. The method of claim 1, wherein, in the reducing spacing step, the one or more side branch channels are constructed and arranged to prevent passage of the droplets.

3. The method of claim 1, wherein the immiscible carrier fluid is added from a direction substantially perpendicular to the main microfluidic channel.

4. The method of claim 1, wherein the immiscible carrier fluid is removed substantially perpendicular to the main microfluidic channel.

5. The method of claim 1, wherein the droplets have the same composition.

6. The method of claim 1, wherein the droplets have different compositions.

7. The method of claim 1, wherein the immiscible carrier fluid is an oil.

8. The method of claim 7, wherein the oil comprises a surfactant.

9. The method of claim 8, wherein the surfactant is a fluorosurfactant.

10. The method of claim 1, wherein the immiscible carrier fluid is a fluorinated oil.

11. The method of claim 1, wherein the immiscible carrier fluid is added using a pump.

12. The method of claim 1, wherein the immiscible carrier fluid is removed using a pump.

13. A method for manipulating droplets of a sample fluid, the method comprising:

flowing droplets of the sample fluid in an immiscible carrier fluid within a main microfluidic channel, wherein the main microfluidic channel comprises a region comprising one or more side branch channels, wherein each droplet is separated from an immediately adjacent droplet by immiscible carrier fluid;

reducing spacing between a pair of immediately adjacent droplets flowing through the region by removing a first volume of immiscible carrier fluid from between only the pair of immediately adjacent droplets via an active flow controllable component operably coupled to a first side branch channel that causes the first volume of the immiscible carrier fluid between only the pair of immediately adjacent droplets to flow into the one or more side branch channels, wherein the pair of immediately adjacent droplets remain intact while flowing through the region and continue to flow within the main microfluidic channel downstream of the region; and increasing the spacing between the pair of immediately adjacent droplets flowing through the region by adding a second volume of immiscible carrier fluid between only the pair of immediately adjacent droplets via a second side branch channel, wherein the pair of immediately adjacent droplets remain intact while flowing through the region and continue to flow within the main microfluidic channel downstream of the region.

* * * * *

UNITED STATES PATENT AND TRADEMARK OFFICE
CERTIFICATE OF CORRECTION

PATENT NO. : 10,054,961 B2
APPLICATION NO. : 14/184312
DATED : August 21, 2018
INVENTOR(S) : Rustem F. Ismagilov, Bo Zheng and Cory J. Gerdts Page 1 of 1

It is certified that error appears in the above-identified patent and that said Letters Patent is hereby corrected as shown below:

In the Specification

In Column 1, please replace the paragraph under the heading "FEDERALLY SPONSORED RESEARCH OR DEVELOPMENT" with the following:
This invention was made with government support under grant number EB001903 awarded by the National Institutes of Health and grant number DMR2011854 awarded by the National Science Foundation. The government has certain rights in the invention.

Signed and Sealed this
Thirteenth Day of September, 2022

Katherine Kelly Vidal
*Director of the United States Patent and Trademark Office*